US012797407B2

(12) United States Patent
Hode et al.

(10) Patent No.: US 12,797,407 B2
(45) Date of Patent: Nov. 17, 2026

(54) SEMI-SYNTHETIC BIOPOLYMERS FOR USE IN STIMULATING THE IMMUNE SYSTEM

(71) Applicant: Immunophotonics, Inc., St. Louis, MO (US)

(72) Inventors: Tomas Hode, St. Louis, MO (US); Siu Kit Lam, St. Peters, MO (US); Joseph Raker, Whitesboro, NY (US); Luciano Alleruzzo, Clayton, MO (US); Robert Nordquist, Oklahoma City, OK (US)

(73) Assignee: Immunophotonics, Inc., Saint Louis, MO (US)

( * ) Notice: Subject to any disclaimer, the term of this patent is extended or adjusted under 35 U.S.C. 154(b) by 584 days.

(21) Appl. No.: 17/598,040

(22) PCT Filed: Jul. 2, 2019

(86) PCT No.: PCT/US2019/040292
§ 371 (c)(1),
(2) Date: Sep. 24, 2021

(87) PCT Pub. No.: WO2020/197578
PCT Pub. Date: Oct. 1, 2020

(65) Prior Publication Data

US 2022/0160753 A1 May 26, 2022

Related U.S. Application Data

(63) Continuation-in-part of application No. 16/367,233, filed on Mar. 27, 2019, now abandoned.

(51) Int. Cl.
*A61K 31/722* (2006.01)
*A61K 39/395* (2006.01)
(Continued)

(52) U.S. Cl.
CPC ........ *A61K 31/722* (2013.01); *A61K 39/3955* (2013.01); *A61K 47/61* (2017.08);
(Continued)

(58) Field of Classification Search
CPC ............................ A61K 31/722; C08B 37/003
See application file for complete search history.

(56) References Cited

U.S. PATENT DOCUMENTS 4,424,346 A 1/1984 Hall et al.
5,095,030 A 3/1992 Levy et al.
(Continued)

FOREIGN PATENT DOCUMENTS

EP 1152013 A1 11/2001
EP 1498128 A1 1/2005
(Continued)

OTHER PUBLICATIONS

U.S. Appl. No. 18/237,228, filed Feb. 0823, Hode; Tomas.*
(Continued)

*Primary Examiner* — Andrea Olson
(74) *Attorney, Agent, or Firm* — Lewis Rice LLC

(57) ABSTRACT

The present relates generally to a method for stimulating the activation of an antigen presenting cell. The method includes activating antigen presenting cells by contacting the cells with an effective amount of a GC polymer that has a molecular weight of less than 420 kDa, followed by determining whether the antigen presenting cells are activated by measuring the amount of co-stimulatory marker CD40 expressed by the cells. Also, the present relates to an injectable pharmaceutical composition for stimulating the activation of an antigen presenting cell.

15 Claims, 15 Drawing Sheets

Molecular weight 1.88 kDa

(51) Int. Cl.
*A61K 47/61* (2017.01)
*A61K 47/64* (2017.01)
*A61P 35/00* (2006.01)

(52) U.S. Cl.
CPC ............ *A61K 47/64* (2017.08); *A61K 47/642* (2017.08); *A61K 47/6425* (2017.08); *A61P 35/00* (2018.01)

(56) References Cited

U.S. PATENT DOCUMENTS

| | | | | |
|---|---|---|---|---|
| 5,214,036 | A | 5/1993 | Allison et al. | |
| 5,258,453 | A | 11/1993 | Kopecek et al. | |
| 5,283,225 | A | 2/1994 | Neumann et al. | |
| 5,314,905 | A | 5/1994 | Pandey et al. | |
| 5,747,475 | A | 5/1998 | Nordquist et al. | |
| 5,773,608 | A | 6/1998 | Yen et al. | |
| 5,912,000 | A | 6/1999 | Podolski et al. | |
| 6,149,671 | A | 11/2000 | Nordquist et al. | |
| 6,290,712 | B1 | 9/2001 | Nordquist et al. | |
| 6,316,007 | B1 | 11/2001 | Nordquist et al. | |
| 6,673,095 | B2 | 1/2004 | Nordquist | |
| 11,111,316 | B2 * | 9/2021 | Hode | C08B 37/003 |
| 11,773,188 | B2 * | 10/2023 | Hode | A61K 39/39558 424/277.1 |
| 12,398,215 | B2 * | 8/2025 | Hode | A61N 5/062 |
| 2002/0022032 | A1 | 2/2002 | Curry et al. | |
| 2004/0047892 | A1 | 3/2004 | Desrosiers et al. | |
| 2004/0192646 | A1 | 9/2004 | Yura et al. | |
| 2005/0106153 | A1 | 5/2005 | Nordouist et al. | |
| 2006/0189573 | A1 | 8/2006 | Nordquist et al. | |
| 2010/0152430 | A1 | 6/2010 | Chen et al. | |
| 2011/0104305 | A1 | 5/2011 | Day et al. | |
| 2013/0330337 | A1 | 12/2013 | Lillard, Jr. | |
| 2015/0018748 | A1 | 1/2015 | Hode et al. | |
| 2016/0206718 | A1 | 7/2016 | Har-Noy | |
| 2017/0106092 | A1 * | 4/2017 | Zaharoff | A61P 35/00 |
| 2017/0306038 | A1 | 10/2017 | Brogdon et al. | |
| 2019/0002594 | A1 | 1/2019 | Hode et al. | |
| 2024/0117075 | A1 * | 4/2024 | Hode | A61P 35/00 |

FOREIGN PATENT DOCUMENTS

| | | | | |
|---|---|---|---|---|
| EP | 2110131 | A1 | 10/2009 | |
| WO | 9631237 | A2 | 10/1996 | |
| WO | 9947162 | A1 | 9/1999 | |
| WO | 0230337 | A2 | 4/2002 | |
| WO | 2002040055 | A2 | 5/2002 | |
| WO | WO-2012166588 | A2 * | 12/2012 | A61P 1/00 |
| WO | 2013109732 | A2 | 7/2013 | |
| WO | 202030571 | A1 | 2/2020 | |

OTHER PUBLICATIONS

Alsaab et al., "PD-1 and PD-L1 Checkpoint Signaling Inhibition for Cancer Immunotherapy: Mechanism, Combinations, and Clinical Outcome" Frontiers in Pharmacology vol. 8 article 561, pp. 1-15, doi: 10.3389/fphar.2017.00561 (Year: 2017).*

Fakhari et al., "Thermoresponsive Gel-Based Formulation for Intratumoral Delivery of Toll-Like Receptor 7/8 Dual Agonist, MEDI9197" Journal of Pharmaceutical Sciences vol. 106 pp. 2037-2045 (Year: 2017).*

Lee et al., "Proton beam therapy and immunotherapy: an emerging partnership for immune activation in non-small cell lung cancer" Transl Lung Cancer Res vol. 2 No. 7 pp. 180-188, doi: 10.21037/tlcr.2018.03.28 (Year: 2018).*

Tallarida et al., "Quantitative Methods for Assessing Drug Synergism" Genes and Cancer vol. 2 No. 11 pp. 1003-1008 DOI: 10.1177/1947601912440575 (Year: 2012).*

Chou, "Drug Combination Studies and Their Synergy Quantification Using the Chou-Talalay Method" Cancer Research vol. 70 No. 2 pp. 440-446, doi: 10.1158/0008-5472-09-Sep. 1947 (Year: 2010).*

Liu et al., "Abstract 4152: Gynergistic gold nanostar-mediated photothermal and immunotherapy for cancer metastasis treatment" Cancer Research vol. 78 13_supplement, DOI:10.1158/1538-7445. AM2018-4152 (Year: 2018).*

Kudo et al., "Immuno-Oncology in Hepatocellular Carcinoma: 2017 Update" Oncology vol. 93 Suppl 1 p. 147, DOI: 10.1159/00048125 (Year: 2017).*

Abdo et al., "Immunotherapy Plus Cryotherapy: Potential Augmented Abscopal Effect for Advanced Cancers" Frontiers in Oncology vol. 8 No. 85 pp. 1-16, DOI:10.3389/fonc.2018.00085 (Year: 2018).*

Yin et al., "A case report of remarkable response to association of radiofrequency ablation with subsequent Atezolizumab in stage IV nonsmall cell lung cancer" Medicine vol. 97:44, DOI:10.1097/MD.0000000000013112 (Year: 2018).*

Murugaiyan, G., et al., "Levels of CD40 Expression on Dendritic Cells Dictate Tumour Growth or Regression", Clinical and Experimental Immunology, May 4, 2007, vol. 149, pp. 194-202.

Nordquist, Robert, et al., "Laser assisted immunotherapy (LIT) for chemotherapy-resistant neoplasms: recent case reports", Progress in Biomedical Optics and Imaging, vol. 8944, Feb. 27, 2014, 1 page.

International Search Report and Written Opinion for International Application No. PCT/US19/40292, mailed Nov. 6, 2019, 20 Pages.

International Preliminary Report on Patentability for International Application PCT/US19/40292, Mail Jul. 2, 2021, 13 Pages.

Extended European Search Report for application No. 19921164.0, Feb. 7, 2023, 13 pages.

Chen et al., "Effect of Different Components of Laser Immunotherapy in Treatment of Metastatic Tumors in Rats," Cancer Research, Aug. 1, 2002, vol. 62, pp. 4295-4299.

Chen et al., "Enhancement of glycated chitosan in laser cancer treatment," Proceedings of SPIE, 2004, vol. 5319, pp. 80-86.

Chen et al., "Laser immunotherapy: a novel treatment modality for metastatic tumors," Molecular biotechnology, 2003, vol. 25, pp. 37-43.

Chen et al., "Laser-photosensitizer assisted immunotherapy: a novel modality for cancer treatment," Cancer Letters, 1997, vol. 115, pp. 25-30.

Chen et al., "Photoimmunotherapy for Cancer Treatment," Journal of Environmental Pathology, Toxicology, and Oncology, 2006, vol. 25, No. 1-2, pp. 281-291.

Donati et al., "The aggregation of pig articular chondrocyte and synthesis of extracellular matrix by a lactose-modified chitosan," Biomaterials, 2005, vol. 26, pp. 987-998.

Extended European Search Report in EP20198582.7, mailed May 10, 2021, 12 pages.

Garrett et al., "Anticancer therapy with checkpoint inhibitors: what, where and when?" Trends in Pharmacological Sciences, May 2011, vol. 32, No. 5, pp. 308-316.

Hogan, M., "The Preparation and Sterilization of Ophthalmic Solutions," California Medicine, Dec. 1949, vol. 71, No. 6, pp. 414-416.

Howling et al., "The effect of chitin and chitosan on the proliferation of human skin fibroblasts and keratinocytes in vitro," Biomaterials, 2001, vol. 22, No. 22, pp. 2959-2966.

Jeon et al., "Antitumor Activity of Chitosan Oligosaccharides Produced in Ultrafiltration Membrane Reactor System," Journal of Microbiology and Biotechnology, 2002, vol. 12, No. 3, pp. 503-507.

Korbelik et al., "Effect of SPG (Sonifilan) immunotherapy and PDT on murine tumor," in: Spinelli et al., Photodynamic Therapy and Biomedical Lasers: Proceedings of the International Conference on Photodynamic Therapy and Medical Laser Applications, Milan, Jun. 24-27, 1992, Amsterdam, Elsevier Science Publishers B.V., 1992, pp. 518-520.

Mi et al., "Synthesis and characterization of a novel glycoconjugated macromolecule," Polymer, 2006, vol. 47, pp. 4348-4358.

Ruel-Gariepy et al., "A thermosensitive chitosan-based hydrogel for the local delivery of paclitaxel," European Journal of Pharmaceutics and Biopharmaceutics, 2004, vol. 57, pp. 53-63.

Sato et al., "In Vivo Drug Release and Antitumor Characteristics of Water-Soluble Conjugates of Mitomycin C with Glycol-Chitosan and N-Succinyl-Chitosan," Biological and Pharmaceutical Bulletin, 1996, vol. 19, No. 9, pp. 1170-1177.

(56) References Cited

OTHER PUBLICATIONS

Sinha et al., "Nanotechnology in cancer therapeutics: bioconjugated nanoparticles for drug delivery," Molecular Cancer Therapeutics, Aug. 2006, vol. 5, No. 8, pp. 1909-1917.
Song et al., "Glycated chitosan as a new non-toxic immunological stimulant, "Immunopharmacology and Immunotoxicology, 2009, vol. 31, No. 2, pp. 202-208.
Ta et al., "Injectable chitosan hydrogels for localised cancer therapy," Journal of Contralled Release, 2008, vol. 126, pp. 205-216.
Tommeraas et al., "Preparation and characterization of branched chitosans," Carbohydrate Polymers, 2011, vol. 83, pp. 1558-1564.
Vodna et al., "Chitosan Based Hydrogel Microspheres as Drug Carriers," Macromolecular Bioscience, 2007, vol. 7, pp. 629-634.
Ying et al., "Preparation, water solubility and antioxidant activity of branched-chain chitosan derivatives," Carbohydrate Polymers, 2011, vol. 83, pp. 1787-1796.
Zhou et al., "InCVAX—A novel strategy for treatment of late-stage, metastatic cancers through photoimmunotherapy induced tumor-specific immunity," Cancer Letters, 2015, vol. 359, pp. 169-177.
Zhou et al., "Immunostimulatory properties of glycated chitosan," Journal of X-Ray Science and Technology, 2011, vol. 19, pp. 285-292.
Zielinska et al., "Nanopharmaceuticals for Eye Administration: Sterilization, Depyrogenation and Clinical Applications," Biology, Oct. 14, 2020, vol. 9, No. 336, 18 pages.
Choi et al., "Radionuclide Therapy," Development of Medical Application Methods Using Radiation, Final Report, Ministry of Science and Technology, Apr. 1998, 171 pages.
Ferri et al., "Chitosan Treatment Induces Changes of Protein Expression Profile and Stilbene Distribution in Vitis vinifera Cell Suspensions," Proteomics, Feb. 2009, vol. 9, No. 3, pp. 610-624.
Office Action issued in KR 1020227005616, mailed Sep. 24, 2023, 6 pages.

* cited by examiner

Molecular weight 1.88 kDa

| Time (minutes) | Test Filter #1 | | | | Test Filter #2 | | | | Test Disc #3 | | | | Control Filter | | | | Temp (°C) |
|---|---|---|---|---|---|---|---|---|---|---|---|---|---|---|---|---|---|
| | Pressure (PSIG) | | | Flow Rate (mL/min.) | Pressure (PSIG) | | | Flow Rate (mL/min.) | Pressure (PSIG) | | | Flow Rate (mL/min.) | Pressure (PSIG) | | | Flow Rate (mL/min.) | |
| | Up Stream | Down Stream | Differential Pressure | | Up Stream | Down Stream | Differential Pressure | | Up Stream | Down Stream | Differential Pressure | | Up Stream | Down Stream | Differential Pressure | | |
| 1 | 57 | <1 | 56 | 2.1 | 57 | <1 | 56 | 2.2 | 57 | <1 | 56 | 3.0 | 22 | <1 | 21 | 3.0 | 26.0 |
| 60 | 57 | <1 | 56 | 2.1 | 57 | <1 | 56 | 2.2 | 57 | <1 | 56 | 3.0 | 23 | <1 | 22 | 3.0 | 26.0 |
| 300 | 57 | <1 | 56 | 1.3 | 57 | <1 | 56 | 1.5 | 57 | <1 | 56 | 2.0 | 23 | <1 | 22 | 2.0 | 26.1 |

FIG. 2

2 Expression of CD40; Formula 1 GC vs. Conventional GC

SEMI-SYNTHETIC BIOPOLYMERS FOR USE IN STIMULATING THE IMMUNE SYSTEM

CROSS REFERENCE TO RELATED APPLICATIONS

This application is a § 371 U.S. National Phase of International Application No. PCT/US2019/040292 filed Jul. 2, 2019, which claims priority from U.S. patent application Ser. No. 16/367,233 filed Mar. 27, 2019. The entire disclosure of all the above documents is herein incorporated by reference.

TECHNICAL FIELD

The present relates generally to semi-synthetic glycated biopolymers, their use in pharmaceutical compositions to treat proliferative disorders (neoplasms). Other uses include, but are not limited to, for example, prophylactic or therapeutic vaccines. More specifically, the present semi-synthetic glycated biopolymers can be used to treat solid cancers, such as carcinoma, sarcoma, and melanoma, in various tissues, for example malignant lung, colon, liver, breast, prostate, pancreas, skin, thyroid and kidney neoplasms, and other types of malignant neoplasms.

BACKGROUND

Proliferative disorders such as cancer can develop in any tissue of any organ at any age. Once an unequivocal diagnosis of cancer is made, treatment decisions become paramount. Though no single treatment approach is applicable to all cancers, successful therapies must be focused on both the primary tumor and its metastases, if present. Historically, local and regional therapy, such as surgery, ablation, or radiation, have been used in cancer treatment, along with systemic therapy, e.g., chemotherapy drugs, or immunotherapy. Despite some success, conventional treatments are not always effective to the degree desired, and the search continues for more efficacious therapies (see, for example, "Cancer immunotherapy: the beginning of the end of cancer?" by Farkona et al. in BMC Medicine (016) 14:73). Thus, there is clearly a significant unmet medical need for more efficient cancer therapies.

Certain biopolymers and their derivatives, which may be produced by, and isolated from, living organisms such as animals, plants, or fungi, display interesting chemical and biological properties that have led to a varied and expanding number of industrial and medical applications. One such biopolymeric derivative is chitosan, which is produced from chitin, a structural component in many organisms for example in exoskeletons in arthropods, such as crustaceans and insects, and as cell walls in fungi. The biopolymer chitin is a linear homopolymer composed of N-acetylglucosamine units joined by β 1→4 glycosidic bonds. Chitosan, which is partially deacetylated chitin, is the most studied of this class of biopolymer-derived compounds. The presence of primary amino groups in chitosan, facilitate a number of approaches for chemical modifications designed mainly to achieve their solubilization and to impart special properties for specific applications.

One such chemical modification is realized via the synthesis of glycated chitosan (GC) and the manufacturing of GCs in which chitosan and a reducing sugar are the starting materials used to manufacture the GC compounds via a reductive amination reaction involving the free amino groups of chitosan and the carbonyl groups of the reducing monosaccharides and/or oligosaccharides.

Conventional GCs, as described in U.S. Pat. No. 5,747,475 ("Chitosan-Derived Biomaterials") and PCT application no. PCT/US13/021903, have shown efficacy in the treatment of metastatic tumor models in animals, although the correlation between chemical structure and composition of GC and immune stimulation has not been fully explored.

However, such conventional GCs are difficult to manufacture, purify and ultimately use in humans. Moreover, conventional GCs, as described in U.S. Pat. No. 5,747,475 are nearly impossible to sterile filter, rendering them unsuitable for industrial manufacturing according to Current Good Manufacturing Practices (cGMP), and therefore unsuitable for human use.

BRIEF SUMMARY

A semi-synthetic biopolymer of Formula 1, as shown below, has a weight-averaged molecular weight ($M_W$) of less than 420 kDa, and has remarkably different properties compared to conventional semi-synthetic biopolymers where the $M_W$ is greater. Indeed, compared to conventional GCs as taught in U.S. Pat. No. 5,747,475 and PCT application no. PCT/US13/021903, we have unexpectedly discovered that the semi-synthetic biopolymer compound of Formula 1, with a $M_W$ of less than 420 KDa, is able to provide significant activation of dendritic cells (DCs) as indicated by increased CD40 expression. Activation of DCs is an important part of inducing a potent anti-tumor T cell response. We believe this activation of DCs can be extrapolated to the use of semisynthetic biopolymers to treat certain proliferative disorders in human subjects.

Accordingly, in one embodiment, there is provided a GC polymer of Formula 1:

Formula 1

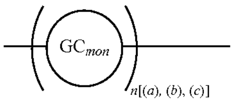

wherein n is the number of subunits and (a), (b) and (c) represent the number of each of the Monomer subunits below comprising $GC_{mon}$:

Monomer (a)

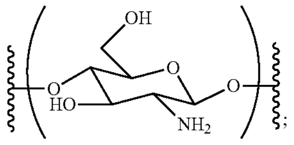

Monomer (b)

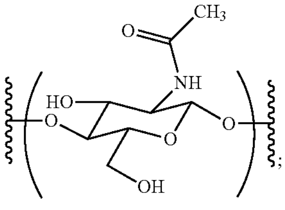

; and

-continued

Monomer (c)

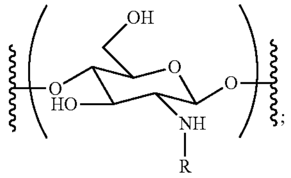

wherein R=substitution resulting from glycation; wherein (n=3–1933, (a)=1–986, (b)=1–386, (c)=1–560) for a $M_W$ of less than 420 kDa; and a DG (Degree of Glycation) of up to, but not including, 30 percent.

In one example, the GC polymer is formulated to produce a sterile filtered aqueous mixture having a pH from between 5 to about 7; and the sterile filtered aqueous mixture having about one percent by weight of the GC polymer dissolved therein so that the sterile filtered aqueous mixture has a viscosity from about one centistoke to approximately one hundred centistokes measured at about 25 degrees Celsius.

In one example, the GC polymer has a molecular weight of less than 420 kDa.

In one example, the GC polymer has a molecular weight of about 250 kDa.

In one example, the GC polymer has a DG of up to but not including 30%.

In one example, the GC polymer in which for a $M_W$ of less than 420 kDa n=3–1933, (a)=1–986, (b)=1–386, (c)=1–560).

In one example, the GC polymer has a $M_W$ of 250 kDa, a DG of 5%, and a DDA of 80%.

In one example, the GC polymer includes at least one of each of the distinct subunits [(a), (b) and (c)].

Accordingly, in another embodiment, there is provided a composition for conditioning a neoplasm using tandem ablation therapy, comprising: an immune stimulant which is a GC polymer of Formula 1, as described above; and wherein the immune stimulant is conjugated to a tumor specific antigen.

Accordingly, in another embodiment, there is provided a composition for conditioning a neoplasm using tandem ablation therapy, comprising an immune stimulant is a GC polymer of Formula 1, as described; and wherein the immune stimulant is conjugated to a cytokine.

Accordingly, in another embodiment, there is provided a composition for conditioning a neoplasm using tandem ablation therapy comprising an immune stimulant, wherein the immune stimulant is conjugated to a TLR agonist, and wherein the immune stimulant is GC polymer of Formula 1, as described above.

In one example, the composition, as described above, in which the tandem ablation therapy is a physical method. The physical method includes heating or freezing the neoplasm. The physical method includes electroporation or embolization of the neoplasm. The composition, as described above, in which the tandem ablation therapy includes immunological treatment Accordingly, in one embodiment there is provided a composition for conditioning a neoplasm using tandem radiation therapy, comprising an immune stimulant, wherein the immune stimulant is conjugated to a tumor specific antigen, and wherein the immune stimulant is a GC polymer of Formula 1, as described above.

Accordingly, in one embodiment there is provided a composition for conditioning a neoplasm using tandem radiation therapy, comprising an immune stimulant, wherein the immune stimulant is conjugated to a cytokine, and wherein the immune stimulant is a GC polymer of Formula 1, as described above.

Accordingly, in one embodiment there is provided a composition for conditioning a neoplasm using tandem radiation therapy, comprising an immune stimulant, wherein the immune stimulant is conjugated to a TLR agonist, and wherein the immune stimulant is a GC polymer of Formula 1, as described above.

In one example, the composition, as described above, in which the tandem radiation therapy includes photon beam therapy, the photon beams being X-rays and gamma rays, or particle beams, the particle beam being proton beams, and in which the tandem radiation therapy includes immunological treatment.

Accordingly, in one embodiment there is provided a composition for conditioning a neoplasm using tandem physical and immunological treatment, comprising an immune stimulant, wherein the immune stimulant is conjugated to a tumor specific antibody and a cytokine, and wherein the immune stimulant is a GC polymer of Formula 1, as described above.

Accordingly, there is provided a composition for conditioning a neoplasm using tandem cytotoxic therapy, and immunological treatment, comprising an immune stimulant, wherein the immune stimulant is conjugated to a tumor specific antigen, and wherein the immune stimulant is a GC polymer of Formula 1, as described above.

Accordingly, in one embodiment there is provided a composition for conditioning a neoplasm using tandem cytotoxic therapy and immunological treatment, comprising an immune stimulant, wherein the immune stimulant is conjugated to a cytokine, and wherein the immune stimulant is a GC polymer of Formula 1, as described above.

Accordingly, in one embodiment there is provided a composition for conditioning a neoplasm using tandem cytotoxic therapy and immunological treatment, comprising an immune stimulant, wherein the immune stimulant is conjugated to a TLR agonist, and wherein the immune stimulant is a GC polymer of Formula 1, as described above.

Accordingly, in one embodiment there is provided a composition for conditioning a neoplasm using tandem physical and immunological treatment, comprising a combination of a chromophore and an immune stimulant, wherein the chromophore and the immune stimulant are conjugated to a tumor specific antibody, and wherein the immune stimulant is a GC polymer of Formula 1, as described above.

In one example, the composition, as described above, in which the GC polymer is used as an immune stimulant to treat cancer treatment.

Accordingly, in one embodiment there is provided a method for treating a neoplasm in a human or other animal host, comprises:

a) selecting an immune stimulant, wherein the immune stimulant comprises a GC polymer of Formula 1, as described above;
b) ablating or irradiating a selected neoplasm whereby neoplastic cellular destruction and immunogenic cell death of the neoplasm is induced, producing fragmented neoplastic tissue and cellular molecules; and
c) introducing the immune stimulant into or around the neoplasm, which stimulates the self-immunological defense system of the host to process the fragmented neoplastic tissue and cellular molecules, such as tumor antigens, and thus create an immunity against the neoplasm.

Accordingly, in one embodiment there is provided a method of producing tumor-specific antibodies in a tumor-bearing host, comprising:

a) ablating or irradiating a tumor to a degree sufficient to induce neoplastic cellular destruction and generating fragmented neoplastic tissue and cellular molecules; and b) introduction of an immune stimulant, the immune stimulant is a GC polymer of Formula 1, as described above, into or around a neoplasm by means of injection so that the host's immune system is stimulated to interact with and process fragmented neoplastic tissue and cellular molecules, upon which a systemic anti-tumor antibody response is induced.

Accordingly, in one embodiment there is provided a method of producing antigen-specific T cells in a tumor-bearing host, comprising:

a) ablating or irradiating a tumor to a degree sufficient to induce neoplastic cellular destruction and generating fragmented neoplastic tissue and cellular molecules; and b) introducing an immune stimulant into or around a neoplasm by means of injection, wherein the immune stimulant being a GC polymer of Formula 1, as described above, so that the host's immune system is stimulated to interact with and process fragmented neoplastic tissue and cellular molecules, upon which a systemic anti-tumor T cell response is induced.

Accordingly, in one embodiment there is provided a method of destroying a neoplasm and concurrently generating an anti-tumor T cell response in a tumor-bearing host, comprising:

(a) selecting an immune stimulant, the immune stimulant being a GC polymer of Formula 1, as described above;

b) ablating or irradiating the neoplasm sufficient to produce a neoplastic cellular destruction and generating fragmented neoplastic tissue and cellular molecules;

c) introducing the immune stimulant into the neoplasm by intratumoral injection, wherein an amalgam of the fragmented tissue and cellular molecules and the immune stimulant is formed at the injection site; and d) stimulating a T cell response against neoplastic cellular tissue within the host.

Accordingly, in one embodiment there is provided a method of destroying a neoplasm and concurrently generating an anti-tumor T cell response in a tumor-bearing host, comprising:

a) selecting a chromophore and an immune stimulant, the immune stimulant being a GC polymer of Formula 1, as described above, the chromophore being suitable to generate either thermal energy or reactive oxygen species upon activation in the visible, near-infrared or infrared wavelength range;

b) introducing the chromophore into the neoplasm by intratumor injection;

c) irradiating the neoplasm with a laser of a wavelength in the visible, near-infrared or infrared range, at a power and for a duration sufficient to activate the chromophore to either produce a photothermal reaction or photochemical reaction inducing neoplastic cellular destruction and generating fragmented neoplastic tissue and cellular molecules;

d) introducing the immune stimulant into the neoplasm by intratumor injection wherein an amalgam of the fragmented tissue and cellular molecules and the immune stimulant is formed; and e) stimulating an anti-tumor immunological response systemically within the host.

In one example, the method further includes conjugating the immune stimulant to a tumor specific antibody, thereby forming a conjugate, and administering the conjugate to the host. The method further includes conjugating the immune stimulant to a tumor specific antigen, thereby forming a conjugate, and administering the conjugate to the host. The conjugate is selected from the group consisting of: cytokines, chemokines, TLR agonists, and proteins, cytotoxic agents; or any combination thereof.

Accordingly, in one embodiment there is provided an injectable pharmaceutical composition for stimulating the activation of an antigen presenting cell comprising:

activating antigen presenting cells by contacting the cells with an effective amount of a GC polymer of Formula 1:

Formula 1

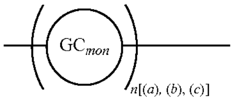

wherein n is the number of subunits and (a), (b) and (c) represent the number of each of the Monomer subunits below comprising $GC_{mon}$:

Monomer (a)

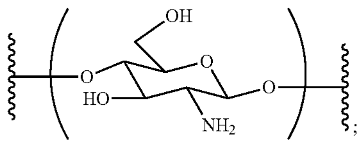

Monomer (b)

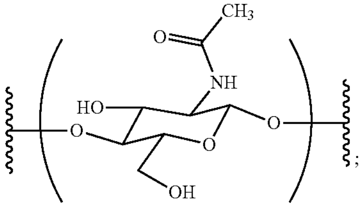

and

Monomer (c)

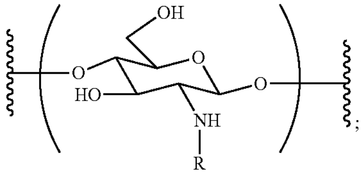

wherein R=substitution resulting from glycation; wherein (n=3-1933, (a)=1-986, (b)=1-386, (c)=1-560) for a $M_W$ of less than 420 kDa; and a DG of up to, but not including, 30 percent; in which the sterile filtered aqueous mixture has a pH from between 5 to about 7; and the sterile filtered aqueous mixture having about one percent by weight of the GC polymer dissolved therein so that the sterile filtered aqueous mixture has a viscosity from about one centistoke to approximately one hundred centistokes measured at about 25 degrees Celsius.

In one example, the sterile filtered aqueous mixture of the GC polymer is an immune stimulant.

In one example, the injectable pharmaceutical composition is formulated for use in treating a neoplasm in conjunction with tumor ablation, radiation therapy, or other means by which immunogenic tumor cell death is achieved.

In one example, the injectable pharmaceutical composition is formulated for use in treating a neoplasm in conjunction with tumor ablation, radiation therapy, or other means by which immunogenic tumor cell death is achieved, and is further combined with administration of a checkpoint inhibitor.

In one example, the immune stimulant is conjugated to a tumor specific antigen.

In one example, the immune stimulant is conjugated to a TLR agonist.

In one example, the immune stimulant is conjugated to a cytokine.

In one example, the immune stimulant is conjugated to a chemokine.

In one example, the immune stimulant is conjugated to a cytotoxic agent.

In one example, the antigen presenting cells are macrophages.

In one example, the antigen presenting cells are dendritic cells.

In one example, the effectiveness of the formula is measured by the amount of co-stimulatory marker, the co-stimulatory marker is CD40.

Accordingly, in one embodiment there is provided a method of stimulating the activation of an antigen presenting cell, the method comprising:

activating antigen presenting cells by contacting the cells with an effective amount of a GC polymer of Formula 1:

Formula 1

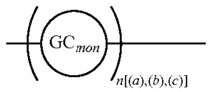

wherein n is the number of subunits and (a), (b) and (c) represent the number of each of the Monomer subunits below comprising $GC_{mon}$:

Monomer (a)

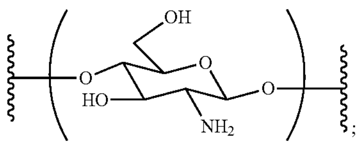

Monomer (b)

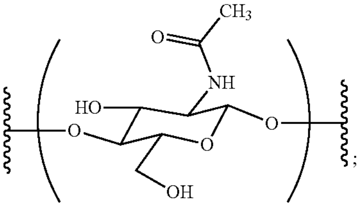

and

-continued

Monomer (c)

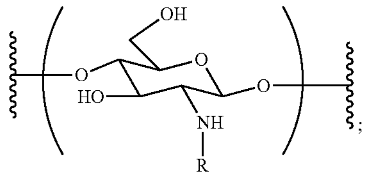

wherein R=substitution resulting from glycation; wherein (n=3-1933, (a)=1-986, (b)=1-386, (c)=1-560) for a $M_W$ of less than 420 kDa; and a DG of up to, but not including, 30 percent; and determining whether the antigen presenting cells are activated by measuring the amount of co-stimulatory marker CD40 expressed by the cells.

In one example, the antigen presenting cells are macrophages.

In one example, the antigen presenting cells are dendritic cells.

In one example, the expression of CD40 causes up-regulation of other co-stimulatory markers. The other co-stimulatory markers include B7 co-stimulatory markers.

In one example, the activation of antigen presenting cells initiate an anti-tumor T cell response.

In one example, the GC polymer has a molecular weight of less than 420 kDa.

In one example, the GC polymer has a molecular weight of about 250 kDa.

In one example, the GC has a DG of up to, but not including, 30%.

In one example, in which for a $M_W$ of less than 420 kDa n=3-1933, (a)=1-986, (b)=1-386, (c)=1-560).

In one example, the GC has a $M_W$ of 250 kDa, a DG of 5%, and a DDA of 80%.

In one example, the GC includes at least 1 of each of the distinct subunits [(a), (b) and (c)].

Accordingly, in another embodiment there is provided use of an immune stimulant, wherein the immune stimulant comprises a GC polymer of Formula 1, as described above, in the treatment of a neoplasm in a human or other animal host, by ablating or irradiating a selected neoplasm whereby neoplastic cellular destruction and immunogenic cell death of the neoplasm is induced, producing fragmented neoplastic tissue and cellular molecules, the immune stimulant being introduced into or around the neoplasm, which stimulates the self-immunological defense system of the host to process the fragmented neoplastic tissue and cellular molecules, such as tumor antigens, and thus create an immunity against the neoplasm.

Accordingly, in another embodiment there is provided use of an immune stimulant, wherein the immune stimulant is a GC polymer of Formula 1, as described above, to produce tumor-specific antibodies in a tumor-bearing host, after ablating or irradiating a tumor to a degree sufficient to induce neoplastic cellular destruction and generating fragmented neoplastic tissue and cellular molecules; introducing the immune stimulant into or around a neoplasm by means of injection so that the host's immune system is stimulated to interact with and process fragmented neoplastic tissue and cellular molecules, upon which a systemic anti-tumor response is induced.

Accordingly, in another embodiment there is provided use of an immune stimulant, wherein the immune stimulant is a GC polymer of Formula 1, as described above, to produce tumor-specific T cells in a tumor-bearing host, after ablating or irradiating a tumor to a degree sufficient to induce neoplastic cellular destruction and generating fragmented neoplastic tissue and cellular molecules, introducing the immune stimulant into or around a neoplasm by means of injection, so that the host's immune system is stimulated to interact with and process fragmented neoplastic tissue and cellular molecules, upon which a systemic anti-tumor T cell response is induced.

Accordingly, in another embodiment there is provided use of an immune stimulant, wherein the immune stimulant is a GC polymer of Formula 1, according to claim 1, to destroy a neoplasm and concurrently generating an anti-tumor T cell response in a tumor-bearing host, by ablating or irradiating the neoplasm sufficient to produce neoplastic cellular destruction and generating fragmented neoplastic tissue and cellular molecule; the immune stimulant being introduced into the neoplasm by intratumoral injection, wherein an amalgam of the fragmented tissue and cellular molecules and the immune stimulant is formed at the injection site; a T cell response against neoplastic cellular tissue within the host being stimulated.

Accordingly, in another embodiment there is provided use of a chromophore and an immune stimulant, the immune stimulant being a GC polymer of Formula 1, to destroy a neoplasm and concurrently generate an anti-tumor T cell response in a tumor-bearing host, the chromophore being suitable to generate either thermal energy or reactive oxygen species upon activation in the visible, near-infrared or infrared wavelength range; the chromophore being introduced into the neoplasm by intratumor injection; the neoplasm being irradiated with a laser of a wavelength in the visible, near-infrared or infrared range, at a power and for a duration sufficient to activate the chromophore to produce a photothermal or photochemical reaction inducing neoplastic cellular destruction and generating fragmented neoplastic tissue and cellular molecules; the immune stimulant being introduced into the neoplasm by intratumor injection wherein an amalgam of the fragmented tissue and cellular molecules and the immune stimulant is formed; and an anti-tumor immunological response being systemically stimulated within the host.

In one example, the use further includes conjugating the immune stimulant to a tumor specific antibody, thereby forming a conjugate, and administering the conjugate to the host.

In one example, the use further includes conjugating the immune stimulant to a tumor specific antigen, thereby forming a conjugate, and administering the conjugate to the host.

In one example, the use in which the conjugate is selected from the group consisting of: cytokines, chemokines, TLR agonists, and proteins, cytotoxic agents; or any combination thereof.

Accordingly, in one embodiment there is provided a method of stimulating the activation of an antigen presenting cell, such as dendritic cells, the method comprising:

activating antigen presenting cells by contacting the cells with an effective amount of a GC polymer of Formula 1:

Formula 1

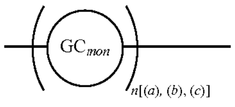

wherein n is the number of subunits, and (a), (b) and (c) represent the number of each of the Monomer subunits below comprising $GC_{mon}$:

Monomer (a)

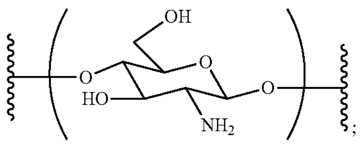

Monomer (b)

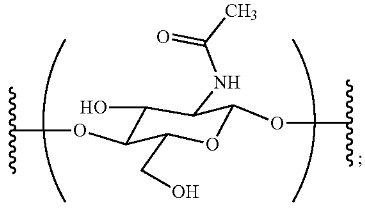

and

Monomer (c)

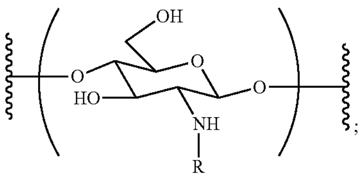

wherein R=substitution resulting from glycation; wherein (n=3-1933, (a)=1-986, (b)=1-386, (c)=1-560) for a $M_W$ of less than 420 kDa; and a degree of glycation (DG) of up, to but not including, 30 percent; and determining whether the antigen presenting cells are activated by measuring the amount of co-stimulatory marker CD40 expressed by the cells.

Accordingly, in another aspect, there is provided an injectable pharmaceutical composition for stimulating the activation of an antigen presenting cell comprising:

activating antigen presenting cells by contacting the cells with an effective amount of a GC polymer of Formula 1:

Formula 1

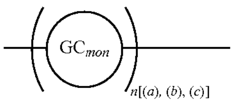

wherein n is the number of subunits and (a), (b) and (c) represent the number of each of the Monomer subunits below comprising $GC_{mon}$:

Monomer (a)

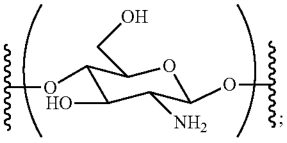

-continued

Monomer (b)

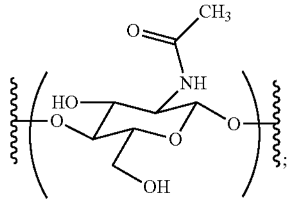

; and

Monomer (c)

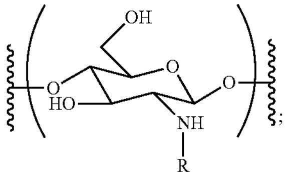

;

wherein R=substitution resulting from glycation; wherein (n=3-1933, (a)=1-986, (b)=1-386, (c)=1-560) for a $M_W$ of less than 420 kDa; and a DG of up to, but not including, 30 percent, in which the sterile filtered aqueous mixture has a pH from between 5 to about 7; and the sterile filtered aqueous mixture having about one percent by weight of the GC polymer dissolved therein so that the sterile filtered aqueous mixture has a viscosity from about one centistoke to approximately one hundred centistokes measured at about 25 degrees Celsius.

Accordingly, in another embodiment, there is provided a composition for use in conditioning a neoplasm using tandem ablation therapy, comprising: an immune stimulant which is a GC polymer of Formula 1, as described above; and wherein the immune stimulant is conjugated to a tumor specific antigen.

Accordingly, in another embodiment, there is provided a composition for use in conditioning a neoplasm using tandem ablation therapy, comprising an immune stimulant is a GC polymer of Formula 1, as described above, and wherein the immune stimulant is conjugated to a cytokine.

Accordingly, in another embodiment, there is provided a composition for use in conditioning a neoplasm using tandem ablation therapy comprising an immune stimulant, wherein the immune stimulant is conjugated to a TLR agonist, and wherein the immune stimulant is GC polymer of Formula 1, as described above.

In one example, the tandem ablation therapy is a physical method.

In one example, the physical method includes heating or freezing the neoplasm.

In one example, the physical method includes electroporation or embolization of the neoplasm.

In another example, the tandem ablation therapy includes immunological treatment.

Accordingly, in another embodiment, there is provided a composition for use in conditioning a neoplasm using tandem radiation therapy, comprising an immune stimulant, wherein the immune stimulant is conjugated to a tumor specific antigen, and wherein the immune stimulant is a GC polymer of Formula 1, as described above.

Accordingly, in another embodiment, there is provided a composition for use in conditioning a neoplasm using tandem radiation therapy, comprising an immune stimulant, wherein the immune stimulant is conjugated to a cytokine, and wherein the immune stimulant is a GC polymer of Formula 1, as described above.

Accordingly, in another embodiment, there is provided a composition for use in conditioning a neoplasm using tandem radiation therapy, comprising an immune stimulant, wherein the immune stimulant is conjugated to a TLR agonist, and wherein the immune stimulant is a GC polymer of Formula 1, as described above.

In one example, the tandem radiation therapy includes photon beam therapy, the photon beam being X-rays and gamma rays, or particle beams, the particle beams being proton beams, and in which the tandem radiation therapy includes immunological treatment.

Accordingly, in another embodiment, there is provided a composition for use in conditioning a neoplasm using tandem physical and immunological treatment, comprising an immune stimulant, wherein the immune stimulant is conjugated to a tumor specific antibody and a cytokine, and wherein the immune stimulant is a GC polymer of Formula 1, as described above.

Accordingly, in another embodiment, there is provided a composition for use in conditioning a neoplasm using tandem cytotoxic therapy, and immunological treatment, comprising an immune stimulant, wherein the immune stimulant is conjugated to a tumor specific antigen, and wherein the immune stimulant is a GC polymer of Formula 1, as described above.

Accordingly, in another embodiment, there is provided a composition for use in conditioning a neoplasm using tandem cytotoxic therapy and immunological treatment, comprising an immune stimulant, wherein the immune stimulant is conjugated to a cytokine, and wherein the immune stimulant is a GC polymer of Formula 1, as described above.

Accordingly, in another embodiment, there is provided a composition for use in conditioning a neoplasm using tandem cytotoxic therapy and immunological treatment, comprising an immune stimulant, wherein the immune stimulant is conjugated to a TLR agonist, and wherein the immune stimulant is a GC polymer of Formula 1, as described above.

Accordingly, in another embodiment, there is provided a composition for use in conditioning a neoplasm using tandem physical and immunological treatment, comprising a combination of a chromophore and an immune stimulant, wherein the chromophore and the immune stimulant are conjugated to a tumor specific antibody, and wherein the immune stimulant is a GC polymer of Formula 1, as described above.

In one example, the GC polymer is used as an immune stimulant to treat cancer.

Accordingly, in another embodiment, there is provided an immune stimulant comprising a GC polymer of Formula 1, as described above, for use in a method for treating a neoplasm in a human or other animal host, the method comprising:

a) ablating or irradiating a selected neoplasm whereby neoplastic cellular destruction and immunogenic cell death of the neoplasm is induced, producing fragmented neoplastic tissue and cellular molecules; and
b) introducing the immune stimulant into or around the neoplasm, which stimulates the self-immunological defense system of the host to process the fragmented neoplastic tissue and cellular molecules, such as tumor antigens, and thus creates an immunity against the neoplasm.

Accordingly, in another embodiment, there is provided an immune stimulant which is a GC polymer of Formula 1, as described above, for use in a method of producing tumor-specific antibodies in a tumor-bearing host, the method comprising:

a) ablating or irradiating a tumor to a degree sufficient to induce neoplastic cellular destruction and generating fragmented neoplastic tissue and cellular molecules; and b) introducing the immune stimulant into or around a neoplasm by means of injection so that the host's immune system is stimulated to interact with and process fragmented neoplastic tissue and cellular molecules, upon which a systemic anti-tumor antibody response is induced.

Accordingly, in another embodiment, there is provided an immune stimulant which is a GC polymer of Formula 1, as described above, for use in a method of producing antigen-specific T cells in a tumor-bearing host, the method comprising:

a) ablating or irradiating a tumor to a degree sufficient to induce neoplastic cellular destruction and generating fragmented neoplastic tissue and cellular molecules; and b) introducing the immune stimulant into or around a neoplasm by means of injection so that the host's immune system is stimulated to interact with and process fragmented neoplastic tissue and cellular molecules, upon which a systemic anti-tumor T cell response is induced.

Accordingly, in another embodiment, there is provided an immune stimulant which is a GC polymer of Formula 1, as described above, for use in a method of destroying a neoplasm and concurrently generating an anti-tumor T cell response in a tumor-bearing host, the method comprising:

a) ablating or irradiating the neoplasm sufficient to produce a neoplastic cellular destruction and generating fragmented neoplastic tissue and cellular molecules;

b) introducing the immune stimulant into the neoplasm by intratumoral injection, wherein an amalgam of the fragmented tissue and cellular molecules and the immune stimulant is formed at the injection site; and c) stimulating a T cell response against neoplastic cellular tissue within the host.

Accordingly, in another embodiment, there is provided a chromophore and an immune stimulant for use in a method of destroying a neoplasm and concurrently generating an anti-tumor T cell response in a tumor-bearing host, said chromophore being suitable to generate either thermal energy or reactive oxygen species upon activation in the visible, near-infrared or infrared wavelength range, and said immune stimulant being a GC polymer of Formula 1, as described above; the method comprising:

a) introducing the chromophore into the neoplasm by intratumor injection;

b) irradiating the neoplasm with a laser of a wavelength in the visible, near-infrared or infrared range, at a power and for a duration sufficient to activate the chromophore to either produce a photothermal reaction or photochemical reaction inducing neoplastic cellular destruction and generating fragmented neoplastic tissue and cellular molecules;

c) introducing the immune stimulant into the neoplasm by intratumor injection wherein an amalgam of the fragmented tissue and cellular molecules and the immune stimulant is formed; and d) stimulating an anti-tumor immunological response systemically within the host.

In one example, the method further includes conjugating the immune stimulant to a tumor specific antibody, thereby forming a conjugate, and administering the conjugate to the host. The method further includes conjugating the immune stimulant to a tumor specific antigen, thereby forming a conjugate, and administering the conjugate to the host. The conjugate is selected from the group consisting of cytokines, chemokines, TLR agonists, and proteins, cytotoxic agents, or any combination thereof.

Accordingly, in another embodiment, there is provided an injectable pharmaceutical composition for use in stimulating the activation of an antigen presenting cell comprising:

activating antigen presenting cells by contacting the cells with an effective amount of a GC polymer of Formula 1:

Formula 1

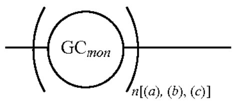

wherein n is the number of subunits and (a), (b) and (c) represent the number of each of the Monomer subunits below comprising $GC_{mon}$:

Monomer (a)

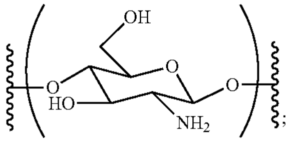

Monomer (b)

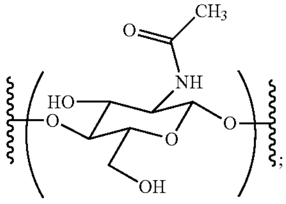

and

Monomer (c)

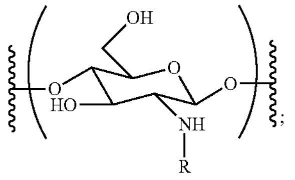

wherein R=substitution resulting from glycation; wherein (n=3-1933, (a)=1-986, (b)=1-386, (c)=1-560) for a $M_W$ of less than 420 kDa; and a DG of up to, but not including, 30 percent; in which the sterile filtered aqueous mixture has a pH from between 5 to about 7; and the sterile filtered aqueous mixture having about one percent by weight of the GC polymer dissolved therein so that the sterile filtered aqueous mixture has a viscosity from about one centistoke to approximately one hundred centistokes measured at about 25 degrees Celsius.

In one example, the sterile filtered aqueous mixture of the GC polymer is an immune stimulant. The injectable pharmaceutical composition is formulated for use in treating a neoplasm in conjunction with tumor ablation, radiation therapy, or other means by which immunogenic tumor cell death is achieved. The injectable pharmaceutical composition is formulated for use in treating a neoplasm in conjunction with tumor ablation, radiation therapy, or other means by which immunogenic tumor cell death is achieved, and which is further combined with administration of a checkpoint inhibitor. The immune stimulant is conjugated to a tumor specific antigen. The immune stimulant is conjugated to a TLR agonist. The immune stimulant is conjugated to a cytokine. The immune stimulant is conjugated to a chemokine. The immune stimulant is conjugated to a cytotoxic agent. The antigen presenting cells are macrophages. The antigen presenting cells are dendritic cells. The effectiveness of the formula is measured by the amount of co-stimulatory marker, the co-stimulatory marker is CD40.

Accordingly, in another embodiment, there is provided a GC polymer, as described above for use in therapy.

Accordingly, in another embodiment, there is provided a GC polymer of Formula 1:

Formula 1

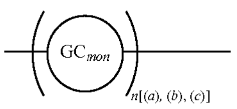

for use in a method of stimulating the activation of an antigen presenting cell, wherein n is the number of subunits and (a), (b) and (c) represent the number of each of the Monomer subunits below comprising $GC_{mon}$:

Monomer (a)

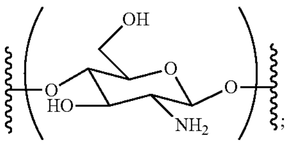

Monomer (b)

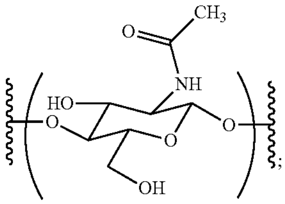

and

Monomer (c)

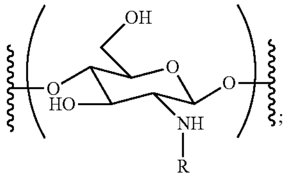

wherein R=substitution resulting from glycation; wherein (n=3-1933, (a)=1-986, (b)=1-386, (c)=1-560) for a $M_W$ of less than 420 kDa; and a DG of up to, but not including, 30 percent, the method comprising:

activating antigen presenting cells by contacting the cells with an effective amount of the GC polymer; and determining whether the antigen presenting cells are activated by measuring the amount of co-stimulatory marker CD40 expressed by the cells.

In one example, the antigen presenting cells are macrophages. The antigen presenting cells are dendritic cells. The expression of CD40 causes up-regulation of other co-stimulatory markers. The other co-stimulatory markers include B7 co-stimulatory markers. The activation of antigen presenting cells initiate an anti-tumor T cell response. The GC polymer has a molecular weight of less than 420 kDa. Alternatively, the GC polymer has a molecular weight of about 250 kDa. The GC has a DG of up to, but not including, 30%. The GC polymer of Formula 1 in which fora $M_W$ of less than 420 kDa n=3-1933, (a)=1-986, (b)=1-386, (c)=1-560). Ideally, Inventor's have contemplated a GC having a $M_W$ of 250 kDa, a DG of 5%, and a DDA of 80%. The GC includes at least 1 of each of the distinct subunits [(a), (b) and (c)] (described above).

Additional aspects and/or advantages of the discovery will be set forth in part in the description which follows and, in part, may be learned by practice of the methods described herein.

BRIEF DESCRIPTION OF THE FIGURES

These and/or other aspects and advantages of the discovery will become apparent and more readily appreciated from the following description, taken in conjunction with the accompanying drawings of which:

FIG. 2 is a Table showing recirculation data from Study #VAL-AM-000754-B of GC of Formula 1, having a $M_W$ of less than 420 kDa.

DETAILED DESCRIPTION

Figure 1:
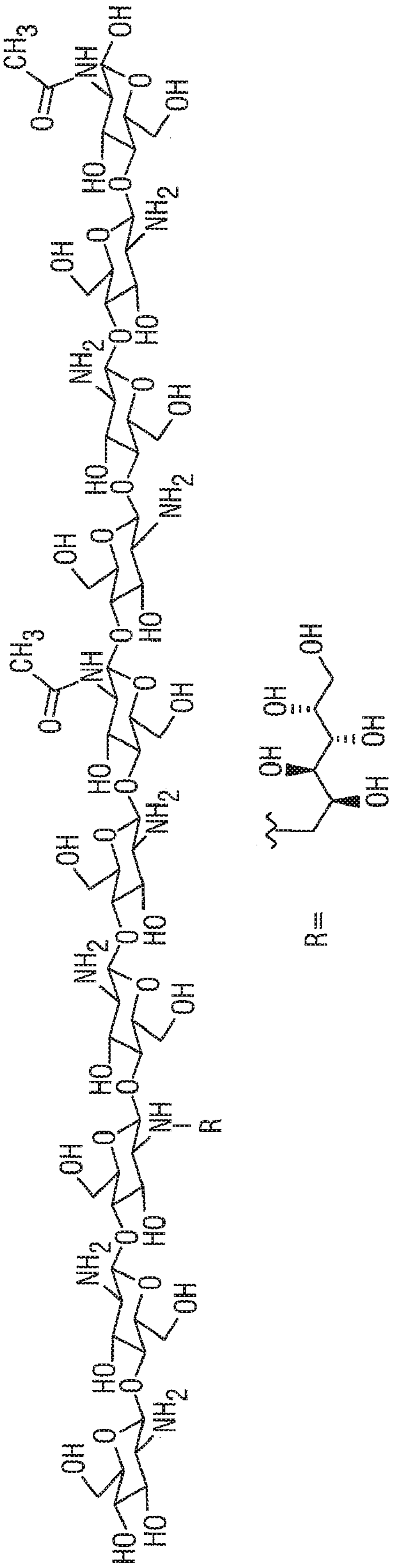
FIG. 1 depicts one small molecular weight example of GC, i.e., galactochitosan (molecular weight=1.88 kDa), where the DG is 10% and the degree of deacetylation (DDA) is 80%.

We, inventors, have unexpectedly discovered that a glycated biopolymer compound of Formula 1 (n=3–2362, (a)=1–1977, (b)=1–495, (c)=1–561), described below, with a $M_W$ value of less than 420 kDa, can stimulate dendritic cells, as compared to conventional GCs with higher $M_W$ values, as measured by CD40 expression, and initiate an anti-tumor T-cell response. We can extrapolate our data to the use of a pharmaceutical composition comprising a compound of Formula 1, to treat proliferative disorders in subjects such as humans. It is to be understood that all references cited herein are incorporated by reference in their entirety.

Definitions

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein the term "and/or" includes any and all combinations of one or more of the associated listed items.

As used herein, the term "consisting of" is intended to mean including and limited to whatever follows the phrase "consisting of". Thus, the phrase "consisting of" indicates that the listed elements are required or mandatory and that no other elements may be present.

As used herein, the term "consisting essentially of" (and grammatical variants thereof) is intended to encompass the recited materials or steps "and those that do not materially affect the basic and novel characteristic(s)". See, *In re Herz,* 537 F.2d 549, 551-52, 190 U.S.P.Q. 461, 463 (COPA 1976) (emphasis in the original); see also MPEP section 2111.03. Thus, the term "consisting essentially of" as used herein should not be interpreted as equivalent to "comprising."

As used herein, the term "glycated chitosan", or "GC", is intended to refer to a product of the glycation, i.e., non-enzymatic glycosylation, of free amino groups of chitosan, followed by stabilization by reduction. Generally speaking, glycation (or non-enzymatic glycosylation) is intended to refer to a process that occurs when a sugar molecule, such as fructose or glucose, binds to a substrate, such as a protein or lipid molecule, without the contributing action of an enzyme. One such example is the non-enzymatic reaction of a sugar and an amine group of a protein to form a glycoprotein. Moreover, we use "GC" and "compounds of Formula 1" interchangeably throughout.

As used herein, the term "physiochemical property" is intended to mean, but is not limited to, any physical, chemical or physical-chemical property of a molecular structure, such as GC. As described further herein, a few examples of these properties are: (i) the $M_W$ of the GC; (ii) the degree of deacetylation (DDA) of the GC; and (iv) the degree of glycation (DG) of the GC.

As used herein, the term "about" is intended to refer to a measurable value such as an amount or concentration (and the like), and is meant to encompass variations of 20%, 10%, 5%, 1%, 0.5%, or even 0.1% of the specified amount As used herein, the sign "~", is intended to refer to a measurable value such as an amount or concentration (and the like), and is meant to encompass variations of 20%, 10%, 5%, 1%, 0.5%, or even 0.1% of the specified amount As used herein the phrase "physiologically compatible" is intended to refer to materials which, when in contact with tissues in the body, are not harmful thereto. The term is intended in this context to include, but is not limited to, aqueous formulations (e.g., solutions) which are approximately isotonic with the physiological environment of interest. Non-isotonic formulations (e.g., solutions) sometimes may also be clinically useful such as, for example dehydrating agents. Additional components of the inventive solutions may include various salts such as, for instance, NaCl, KCl, $CaCl_2$, $MgCl_2$ and Na based buffers.

As used herein, the term "immune stimulant" is intended to refer to any molecule, composition or substance that acts to enhance the immune system's ability to respond to an antigen; for instance, GC which acts to enhance the immune system's ability to respond to a tumor antigen.

As used herein the term "substantially aqueous" is intended to mean that the formulations or preparations, in certain aspects, may include some percentage of one or more non-aqueous components, and one or more pharmaceutically acceptable excipients.

As used herein, the term "checkpoint inhibitor" is intended to mean molecules, in one example, monoclonal antibodies, that inhibit the interactions between checkpoint molecules and theft ligands. Certain checkpoint molecules' engagement on a T cell is a natural mechanism to dampen/shut down the effector T cell functions. Thus, the checkpoint inhibitor can be construed as releasing or at least causing immune suppression.

Compounds

We, inventors, have made a surprising and unexpected discovery that a semi-synthetic biopolymer of Formula 1 (n=3–2362, (a)=1–1977, (b)=1–495, (c)=1–561), described above and below, with a $M_W$ of less than 420 kDa, is able to stimulate dendritic cells resulting in CD40 expression, as compared to conventional GCs with greater $M_W$ values, and thereafter stimulate a potent anti-tumor response. We believe these data can be extrapolated to use of the semisynthetic biopolymer to treat certain proliferative disorders in human subjects.

The generic structure, Formula 1, is shown above and below, and will be used throughout the description herein to describe various GCs. GCs are semisynthetic polymers that contain at least 1 of each of the following 3 distinct monomers, including but not limited to: glucosamine [monomer (a)]; N-acetylglucosamine [monomer (b)]; and, N-glycated glucosamine [monomer (c)]. Formula 1 provides a generic polymeric structure for GCs, containing n number of monomers, with that set of monomers being comprised of specified numbers of the individual monomers (a), (b) and (c). Furthermore, descriptions of specific compounds will also include values of the weight-averaged molecular weight ($M_W$) which is the industry standard for reporting the molecular mass of polymeric mixtures. Additional descriptors may include the degree of glycation (DG) and the degree of deacetylation (DDA) which are values for the percentage of glycated glucosamine and all monomers which are not N-acetylglucosamine, respectively. As polymer mixtures often contain polymer chains of varying molecular weight and the methods of determination of $M_W$ rely on secondary and tertiary structural characteristics of the polymer chains, the reported values of $M_W$ can be assumed to vary ±15% (in line with United States Pharmocopeia guidelines).

Core:

Generally speaking, the core of the semi-synthetic biopolymer, which is shown above in Formula 1, is comprised of series of monomers ($GC_{mon}$) shown within the parentheses, which comprise the total number of monomers defined by the integer n:

Formula 1

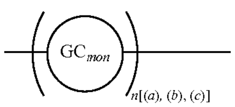

wherein n is the number of subunits and (a), (b) and (c) represent the number of each of the Monomer subunits below comprising $GC_{mon}$:

Monomer (a)

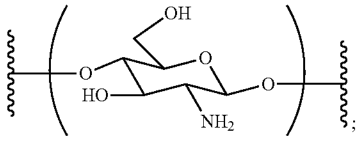

Monomer (b)

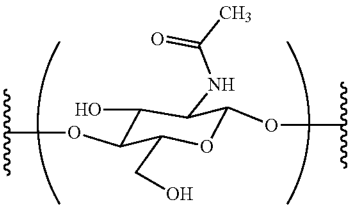

and

Monomer (c)

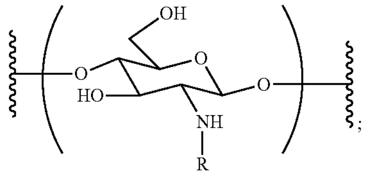

wherein R=substitution resulting from glycation.

In one aspect, the $GC_{mon}$ portion of the Formula 1 includes one or more of each the monomeric subunits (a), (b) and (c). Generally speaking, the semi-synthetic biopolymer, is comprised of varying numbers of the monomers (a), (b) and (c) (Formula 1).

Any and each individual definition of Core as set out herein may be combined with any and each individual definition of n, Mw, DDA, and DG, as set out herein.

Integer n:

Formula 1 represents a generic formula of the semi-synthetic biopolymer in which "n" is an integer representing the number of monomers. A small molecular weight example of galactated chitosan (1.88 kDa) is provided in FIG. 1 as a specific example of Formula 1 and to demonstrate the connectivity of the polymer strands.

For the structure in FIG. 1, n=10, indicating 10 monomers.

For the structure in FIG. 1, (a)=8, indicating 8 glucosamine monomers.

For the structure in FIG. 1, (b)=2, indicating 2 N-acetylglucosamine monomers and a DDA of 80%.

For the structure in FIG. 1, (c)=1, R=galactoyl, indicating 1 N-glycated glucosamine monomers and a DG of 10%

Glycated chitosan (GC) is a polymer that consists only of three distinct subunits [(a), (b) and (c), Formula 1]

GC must contain at least 1 of each of the distinct subunits [(a), (b) and (c)].

In one example, the GC has a $M_W$ of less than 420 kDa

In another example, the GC has a $M_W$ of about 250 kDa

In another example, the GC has a DG of up to, but not including, 30%.

The integer 'n' defines the number of monomers ($GC_{mon}$), as shown in Formula 1.

Any and each individual definition of 'n' as set out herein may be combined with any and each individual definition of Core, Mw, DDA, and DG, as set out herein.

Weight-Averaged Molecular Weight (Mw):

$M_W$ is the measured molecular weight average of a polymer sample with preference given to chains of higher molecular weights. For a sample with a reported $M_W$ value, there is an equal mass of molecules distributed around that value. $M_W$ is most commonly measured through light scattering techniques, which are sensitive to molecular size.

It should be understood that compounds of Formula 1, contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present is intended to include all such possible isomers, as well as, their racemic and optically pure forms. Optically active (+) and (−), (R)- and (S), or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively, specific enantiomers may be synthesized by asymmetric synthesis using optically active reagents, substrates, catalysts, or solvents or by converting one enantiomer to another by asymmetric transformation.

Certain compounds of Formula 1 may exist as a mix of epimers. Epimers means diastereoisomers that have the opposite configuration at only one of two or more stereogenic centers present in the respective compound.

Furthermore, certain compounds of Formula 1 may exist in zwitterionic form and the present includes zwitterionic forms of these compounds and mixtures thereof.

Any and each individual definition of Mw as set out herein may be combined with any and each individual definition of Core, n, DDA, and DG, as set out herein.

Mw of the GC

Any number of suitable techniques in the chemical arts can be used to reliably and accurately determine the weight-averaged molecular weight ($M_W$) of the GC.

An example of a GC is prepared as an injectable formulation comprising GC with a weight-averaged molecular weight (MW) less than 420 kDa.

In certain specific aspects, 'n' is an integer of from about 3 to about 2362 for a $M_W$ range of less than 420 kDa.

Degree of Deacetylation (DDA) of GC

Another property of GCs represented by Formula 1 is the degree of deacetylation (DDA). Any number of suitable techniques in the chemical arts can be used to reliably and accurately determine the degree of deacetylation of GCs.

NMR is one technique that can be used to determine the DDA of GCs.

Any and each individual definition of DDA as set out herein may be combined with any and each individual definition of Core, n, Mw, and DG, as set out herein.

Degree of Glycation (DG) of GC

Another property of GC represented by Formula 1 is the degree of glycation (DG). Any number of suitable techniques in the chemical arts can be used to reliably and accurately determine the DG of GCs.

NMR is one technique that can be used to determine the DG of GCs. Furthermore, NMR can be used to characterize other chemical characteristics of GCs Carbon/nitrogen (C/N) elemental combustion analysis is another technique that can be used to determine the DG of the GCs by means of comparing the C/N ratio of GC vs. the chitosan starting material Enzymatic digestion coupled with HPLC is yet another technique that can be used to determine the DG of GCs.

It is to be understood that other suitable analytical methods and instrumentation can also be used for simultaneous detection, measurement and identification of multiple components in a sample.

Colorimetric measurement of derivatives of GCs can be used to determine the DG, such as via a ninhydrin reaction.

It has thus been found that GCs having desired values of $M_W$, DDA and DG to provide unexpected and advantageous improvements in biological activity and sterile filterability.

Specific examples of the above include the following:

Monomer a-Monomer a-Monomer-a is chitosan; and

Monomer b-Monomer-b-Monomer-b is chitin

Any and each individual definition of DG as set out herein may be combined with any and each individual definition of Core, n, Mw, and DDA, as set out herein.

Exemplary Methods for Determination of Viscosity, No Relation to Sterile Filterability Any number of suitable techniques in the chemical arts can be used to reliably and accurately determine viscosity of a GC formulation.

It is to be understood that viscosity can be reliably measured with various types of instruments, e.g., viscometers and rheometers. A rheometer is used for those fluids which cannot be defined by a single value of viscosity and therefore require more parameters to be set and measured than is the case for a viscometer. Close temperature control of the fluid is essential to accurate measurements, particularly in materials like lubricants, whose viscosity can double with a change of only 5° C.

Accordingly, the viscosity of a GC can be determined according to any suitable method known in the art.

For instance, viscosity can be reliably measured in units of centipoise. The poise is a unit of dynamic viscosity in the centimeter gram second system of units. A centipoise is one one-hundredth of a poise, and one millipascal-second (mPa·s) in SI units (1 $cP=10^{-2}$ $P=10^{-3}$ Pa·s). Centipoise is properly abbreviated cP, but the alternative abbreviations cps, cp, and cPs are also commonly seen. A viscometer can be used to measure centipoise. When determining centipoise, it is typical that all other fluids are calibrated to the viscosity of water.

Exemplary Determination of Viscosity

There are numerous factors that affect the viscosity of solutions and, in particular, solutions of polymers, other than molecular weight. In the case of GC, the injectability of solutions of GC is highly dependent upon the viscosity and rheological properties of the GC in solution. These properties are, in turn, highly dependent upon the molecular weight, DG and DDA of the GC. These properties affect the secondary and tertiary solution structures of the GC molecules, contributing significantly to the viscosity and rheological properties of solutions prepared therefrom.

It has been noted that the improved viscosity and rheological properties of GCs are, in turn, highly dependent upon particular chemical properties of the GC.

Synthetic Methodology

Semi-synthetic biopolymers such as those described above can be synthesized via a reductive amination reaction involving the free amino groups of chitosan and the carbonyl groups of reducing monosaccharides and/or oligosaccharides. This reaction is a 2-step process, involving first the formation of an imine between the chitosan and the reducing sugar, followed by reduction of the imine to the amine using a wide range of reducing agents. The products of the first step of the reaction, which mainly are a mixture of Schiff bases (i.e. the carbon atom from the carbonyl group is now doubly bonded to the nitrogen from the free amine releasing one molecule of water) and Amadori products (i.e. the carbon atom of said carbonyl group is singly bonded to the nitrogen atom of said amino group while an adjacent carbon atom is double bonded to an oxygen atom) may be used as such or after the second step of the reaction, the stabilization by reduction with hydrides, such as boron-hydride reducing agents, for example $NaBH_4$, $NaBH_3CN$, $NaBH(OAc)_3$, etc., or by exposure to hydrogen in the presence of suitable catalysts.

GC is a product of the glycation (i.e., non-enzymatic glycosylation) of free amino groups of chitosan, followed by stabilization by reduction. Glycation endows the chitosan with advantageous solubility and viscosity characteristics which facilitate the use of the derivative in conjunction with laser-assisted immunotherapy and other applications of the derivative.

Chitosan and a reducing sugar are the starting materials used to manufacture compounds of Formula 1. The presence of primary amino groups in chitosan, facilitate a number of approaches for chemical modifications designed mainly to achieve their solubilization and to impart special properties for specific applications.

Solubilization of the starting material chitosan can be achieved by dissolution in aqueous acidic solutions, both organic and inorganic, leading to the formation of water soluble chitosonium salts by protonation of the free amino groups. Modifications of the amino groups of chitosan include the introduction of chemical groups such as carboxymethyl, glyceryl, N-hydroxybutyl and others. Glycation, i.e., non-enzymatic glycosylation of the free amino groups of chitosan, followed by stabilization by reduction, offers a desired approach for the preparation of various pharmaceutical formulations utilized herein.

The GC described herein is in the form of a Schiff base, an Amadori product, or in one example, in their reduced secondary amine or alcohol, respectively. In another example, the GC includes a carbonyl reactive group. It is desired that GC described herein is obtained by reacting chitosan with a monosaccharide and/or oligosaccharide, in one example in the presence of an acidifying agent, for a time sufficient to accomplish Schiff base formation between the carbonyl group of the sugar and the primary amino groups of chitosan (also referred to herein as glycation of the amino group) is in one example followed by stabilization by reduction of Schiff bases and of their rearranged derivatives (Amadori products) to the secondary amines or alcohols, in one example providing a DG of up to, but not including, 30%.

The present is the first demonstration whereby up to, but not including, 30% glycation of the chitosan polymer is achieved. Thus, according to one example, a GC formulation, consisting essentially of GC polymer, wherein the GC polymer has a molecular weight less than 420 kDa, and further wherein the GC polymer possesses up to, but not including, (30) thirty percent glycation.

The products resulting from the non-enzymatic glycosylation of free amino groups of chitosan are thus mainly a mixture of Schiff bases, i.e. the carbon atom of the initial carbonyl group double bonded to the nitrogen atom of the amino group (also known as the imine functional group), and Amadori products, i.e. the carbon atom of the initial carbonyl group bonded to the nitrogen atom of said amino group by a single bond while an adjacent carbon atom is double bonded to an oxygen atom forming a ketone group. These products (resulting from the non-enzymatic glycosylation process) may be used as such, or after stabilization by reduction with hydrides, such as boron-hydride reducing agents, for example $NaBH_4$, $NaBH_3CN$, $NaBH(OAc)_3$, and the like, or by exposure to hydrogen in the presence of suitable catalysts.

Various products obtained by chitosan glycation will be utilized as such or reacted with other natural or synthetic materials, e.g., reaction of aldehyde-containing derivatives of GC with substances containing two or more free amino groups, such as on the side chains of amino acids rich in lysine residues as in collagen, on hexosamine residues as in chitosan and deacetylated glycoconjugates, or on natural and synthetic diamines and polyamines. This is expected to generate crosslinking through Schiff base formation and subsequent rearrangements, condensation, dehydration, etc. Stabilization of modified GC materials can be made by chemical reduction or by curing involving rearrangements, condensation or dehydration, either spontaneous or by incubation under various conditions of temperature, humidity and pressure. The chemistry of Amadori rearrangements, Schiff bases and the Leukart-Wallach reaction are detailed in The Merck Index, Ninth Edition (1976) pp. ONR-3, ONR-55 and ONR-80, Library of Congress Card No. 76-27231, the same being incorporated herein by reference. The chemistry of nucleophilic addition reactions as applicable to the present invention is detailed in Chapter 19 of Morrison and Boyd, Organic Chemistry, Second Edition (eighth printing 1970), Library of Congress Card No. 66-25695, the same being incorporated herein by reference.

As further described herein, particular types (e.g., particular types of reducing sugars) and degrees of glycation have surprisingly been found to endow the GC with unexpected and advantageous characteristics that facilitate the use of the GC in conjunction with tumor ablation, radiation therapy, cytotoxic agents, checkpoint inhibitors such as anti-PD-1 and PD-L1 antibodies, adoptive immunity transfer, cytokine therapy, and other therapeutic applications.

The D-galactose derivative of GC is particularly desired insofar as D-galactose has a relatively higher naturally occurring incidence of its open chain form. The GC may be prepared in any number of suitable formulations including, for example, a solid form, as a viscous formulation, or in any other suitable form.

In accordance with the present invention, chitosan may be non-enzymatically glycated utilizing any of a number of the same or different reducing sugars, e.g., the same or different monosaccharides and/or oligosaccharides. Examples of such monosaccharide glycosylation agents include the following D and L-isomers: trioses, tetroses, pentoses, hexoses, heptoses, and the like, such as glucose, galactose, fructose, mannose, allose, altrose, idose, talose, fucose, arabinose, gulose, hammelose, lyxose, ribose, rhamnose, threose, xylose, psicose, sorbose, tagatose, glyceraldehyde, dihydroxyacetone, erythrose, threose, erythrulose, mannoheptulose, sedoheptulose and the like. Suitable oligosaccharides include the fructo-oligosaccharides (FOS), the galacto-oligosaccharides (GOS), the mannan-oligosaccharides (MOS) and the like.

Combination Therapies

Compounds of Formula 1 may be combined with any of a number of other therapies for cancer, including, but limited to, adoptive T cell transfer therapy, tumor-infiltrating cell therapy, oncolytic viruses, cancer vaccines/dendritic cell-based therapies, and checkpoint blockade:

Adoptive T cell transfer, such as chimeric antigen receptor T cells CAR T or TCR gene-modified T cell therapy include the following non-limiting potential "target" or "receptor" examples which may interact either agonistically or antagonistically with one or more known pharmaceutical entities.

ErbB dimers, IL4; CD19; GPC3; CD133; BOMA; Kappa light chains; CD30; IL13Ra2; NY-ESO-1 and HLA-A2: E6; and MAGE-A10.

The following are non-limiting examples of tumor infiltrating cell therapies: TIL and MIL The following are non-limiting examples of cancer vaccines targeting specific cancers or tumor associated antigens/receptors, and dendritic cell-based therapies that utilizes:

Prostate cancer; lung adenocarcinoma cells; gastric cancer cells; melanoma antigens; VEGFR-2, prostate cancer antigens; human telomerase; PAP; E7 antigen; MAGE-A3; Her2; NY-ESO01; brachyury; BPX101; WT-1-expressing tumors; survivin-expressing tumors; HSP70 and GPC3; HSP96; URLC10, CDCA1, KOC1; MDA-5 and NOXA; and Gp 100; and personal tumor neoantigens that can be identified on a case to case basis.

The following are non-limiting examples of oncolytic viruses:

T-VEC; Coxsackievirus A21 (CVA21-CAVATAK); Pelareorep (Reolysin); DNX-2401; Enadenotucirev (EnAd); LOAd703; GL-ONC1; and Pexa-Vec.

The following is a non-limiting list of checkpoint inhibitor drug types, which include PD-1 inhibitors; PD-L1 inhibitors; and CTLA-4 inhibitors.

The following are non-limiting examples of other potential targets in anti-cancer therapy, and where drugs designed to antagonize (inhibit) or agonize (stimulate) such targets may be combined with compounds of Formula 1 described herein:

IDO1; LAG-3 (CD223); TIM-3; TIGIT; VISTA; B7-H3 (CD276); KIR; A2aR; TGF-β; PI3Kγ; CD47; CD73; OX40; GITR; ICOS; 4-1BB (CD137); CD27-CD70; and CD40.

Conjugations and Admixtures

It is also to be understood that the compounds of Formula 1 may be conjugated or admixed with any of a number of agonists for TLR, IDO, arginase, STING and pathways that stimulate the maturation of antigen presenting cells, including the following non-limiting examples of TLR:

TLR1-TLR2; TLR2-TLR6; TLR9; TLR3: TLR-4; TLR7: TLR5; TLR7-TLR8; TLR104; IDO; and arginase.

Moreover, compounds of Formula 1 may be conjugated or admixed with any of a number of other immunoadjuvants or immune stimulants, non-limiting examples of which include:

Delivery systems like Alum adjuvants, calcium phosphate, liposomes, virosomes/virus like particles; Emulsions; Squalenes; Saponin-based chemicals; Mineral salts; Polymeric microsphere/nanoparticles; carbohydrate-based adjuvants; Bacterial products/components; and the combinations thereof.

Compounds of Formula 1 may be conjugated or admixed with any of a number of cytokines or cytokine derivatives/gene therapy, selected from the following non-limiting examples:

IL-1a, IL1-b, IL-1Ra, IL-2, IL-3, IL-4, IL-5, IL-6, IL-7, IL-8, IL-9, IL-10, IL-11, IL-12, IL-13, IL-14, IL-15, IL-16, IL-17A, IL-17B,C,D, IL-17-F, IL-18, IL-19, IL-20, IL-21, IL-22, IL-23, IL-24, IL-25(IL-17E), IL-26, IL-27 (p281EB13), IL-28A/B/IL29, IL-30 (p28 subunit of IL-27), IL-31, IL-32, IL-33, IL-34, IL-35 (p351EB13), IL-36, IL-37, IL-38, IFNa, IFNb, IFNg, TGFb, TNFa, GM-CSF, M-CSF, Ad-RTS-hIL-12, and NKTR-214.

Compounds of Formula 1 may also be conjugated or admixed with any of a number of chemokines, selected from the following non-limiting examples:

CXCL1, CXCL2, CXCL3, CXCL4, CXCL5, CXCL6, CXCL7, CXCL8, CXCL9, CXCL10, CXCL11, CXCL12, CXCL13, CXCL14, Cxcl15, CXCL16, CCL1, CCL2, CCL3, CCL4, CCL5, CCL6, CCL7, CCL8, CCL9/10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, and CX3CL1.

Compounds of Formula 1 may be conjugated or mixed with any of a number of antigens.

Major classes of tumor antigens include, but not limited to: tissue differentiation antigens such as MART-1, gp100, CEA, CD19; tumor germline (tumor/testis) antigens such as NY-ESO-1, MAGE-A3; normal proteins overexpressed by cancer cells such as hTERT, EGFR, Mesothelin; viral proteins such as HPV, EBV, MCC; tumor-specific mutated antigens such as Mum-1, β-catenein, CDK4, ERBB2IP; tumor associated carbohydrate antigens such as GM2, GD2, sTn, MUC-1, globo-H, and the like.

Selected examples of tumor antigens are listed below (with synonyms and source of antigens excluded):

ERBB2, BIRC5, CEACAM5, WDR46, BAGE, CSAG2, DCT, MAGED4, GAGE1, GAGE2, GAGE3, GAGE4, GAGE5, GAGE6, GAGE7, GAGE8, IL13RA2, MAGEA1, MAGEA2, MAGEA3, MAGEA4, MAGEA6, MAGEA9, MAGEA10, MAGEA12, MAGEB1, MAGEB2, MAGEC2, TP53, TYR, TYRP1, SAGE1, SYCP1, SSX2, SSX4, KRAS, PRAME, NRAS, ACTN4, CTNNB1, CASP8, CDC27, CDK4, EEF2, FN1, HSPA1B, LPGAT1, ME1, HHAT, TRAPPC1, MUM3, MYO1B, PAPOLG, OS9, PTPRK, TPI1, ADFP, AFP, AIM2, ANXA2, ART4, CLCA2, CPSF1, PPIB, EPHA2, EPHA3, FGF5, CA9, TERT, MGAT5, CEL, F4.2, CAN, ETV6, BIRC7, CSF1, OGT, MUC1, MUC2, MUM1, CTAG1, CTAG2, CAMEL, MRPL28, FOLH1, RAGE, SFMBT1, KAAG1, SART1, TSPYL1, SART3, SOX10, TRG, WT1, TACSTD1, SILV, SCGB2A2, MC1R, MLANA, GPR143, OCA2, KLK3, SUPT7L, ARTC1, BRAF, CASP5, CDKN2A, UBXD5, EFTUD2, GPNMB, NFYC, PRDX5, ZUBR1, SIRT2, SNRPD1, HERV-K-MEL, CXorf61, CCDC110, VENTXP1, SPA17, KLK4, ANKRD30A, RAB38, CCND1, CYP1B1, MDM2, MMP2, ZNF395, RNF43, SCRN1, STEAP1, 707-AP, TGFBR2, PXDNL, AKAP13, PRTN3, PSCA, RHAMM, ACPP, ACRBP, LCK, RCVRN, RPS2, RPL10A, SLC45A3, BCL2L1, DKK1, ENAH, CSPG4, RGS5, BCR, BCR-ABL, ABL-BCR, DEK, DEK-CAN, ETV6-AML1, LDLR-FUT, NPM1-ALK1, PML-RARA, SYT-SSX1, SYT-SSX2, FLT3, ABL1, AML1, LDLR, FUT1, NPM1, ALK, PML1 RARA SYT, SSX1, MSLN UBE2V1, HNRPL, WHSC2, EIF4EBP1, WNK2, OAS3, BCL-2, MCL1, CTSH, ABCC3, BST2, MFGE8, TPBG, FMOD, XAGE1, RPSA, COTL1, CALR3, PA2G4, EZH2, FMNL1, HPSE, APC, UBE2A, BCAP31, TOP2A, TOP2B, ITGB8, RPA1, ABI2, CCNI, CDC2, SEPT2, STAT1, LRP1, ADAM17, JUP, DDR1, ITPR2, HMOX1, TPM4, BAAT, DNAJC8, TAPBP, LGALS3BP, PAGE4, PAK2, CDKN1A, PTHLH, SOX2, SOX11, TRPM8, TYMS, ATIC, PGK1, SOX4, TOR3A, TRGC2, BTBD2, SLBP, EGFR, IER3, TTK, LY6K, IGF2BP3, GPC3, SLC35A4, HSMD, H3F3A, ALDH1A1, MFI2, MMP14, SDCBP, PARP12, MET, CCNB1, PAX3-FKHR, PAX3, FOXO1, XBP1, SYND1, ETV5, HSPA1A, HMHA1, TRIM68, ACSM2A, ATR, USB1, RTCB, C6ORF89, CDC25A, CDK12, CRYBA1, CSNK1A1, DSCAML1, F2R, FNDC3B, GAS7, HAUS3, HERC1, HMGN2, SZT2, LRRC41, MATN2, NIN, PLEKHM2, POLR2A, PPP1R3B, RALGAPB, SF3B1, SLC46A1, STRAP, SYT15, TBC1D9B, THNSL2, THOC6, WHSC1L1, XPO1, BCL11A, SPEN, VPS13D, SOGA1, MAP1A, ZNF219, SYNPO, NFATC2, NCBP3, HIVEP2, NCOA1, LPP, ARID1B, SYNM, SVIL, SRRM2, RREB1, EP300, RCSD1, CEP95, IP6K1, RSRP1, MYL9, TBC1D10C, MACF1, MAP7D1 MORC2, RBM14, GRM5, NIFK, TLK1, IRS2, PPP1CA, GPSM3, SIK1, HMGN1, MAP3K11, GFI1, KANSL3, KLF2, CCDC88B, TNS3, N4BP2 TPX2, KMT2A SRSF7 GRK2, GIGYF2, SOAP, MIIP, ZC3H14, ZNF106, SKI, SETD2, ATXN2L, SRSF8, LUZP1, KLF10, RERE, MEF2D, PCBP2 LSP1, MEFV, ARHGAP30, CHAF1A, FAM53C, ARHGAP17, HSPB1, NCOR2 ATXN2, RBM15, RBM17 SON, TSC22D4, MYC, and ANKRD17.

The conjugation or admixture may include the addition of one antibody before the compound of Formula 1; addition of the antibody after the compound of Formula 1; or the addition of the antibody and the compound of Formula 1 simultaneously.

As is known in the art, antibodies are the excreted form of B-cell receptor (BCR) and so they have essentially the same level of diversity as BCR, which can reach $10^{17}$. Some antibodies have been isolated and thereafter manufactured as therapeutic agents for human use.

Compounds of Formula 1 may be conjugated or admixed with any of a number of antibodies including the following non-limiting monoclonal antibodies and bispecific antibodies:

Monoclonal antibodies and so-called "bi-specific" antibodies have been developed for use as anti-cancer therapeutic agents. The antibodies employ different mechanisms of action leading to cancer cell death, either by direct tumor killing, immune mediated tumor cell killing, vascular/stromal ablation, secondary effector cells/molecules/cytotoxic agents initiated by the antibodies or other indirect mechanisms. As the tumor cells are killed, antigens are released. Without wishing to be bound by theory, administration of a compound of Formula 1 to a subject, specifically a human subject, may magnify the resulting immune response via steps described above.

The following are non-limiting examples of targets against which monoclonal antibodies have been used for cancer therapy:

HER2; VEGF; EGFR; CD20; CD30; and CD33.

The following are non-limiting examples of targets used to generate Antibody Drug conjugates:

c-Met; gpNMB; EGFR; Folate receptor alpha (FRα); Nectin-4; Trop-2; CD22; CEACAM; CD56; DLL3; CD25; GCC; HER2; GPNMB; CA-6; LIV-1; Tyrosine kinase 7; Ephrin-A4; LAMP-1; P-cadherin 3; HER3; Axl; PMSA; PD-1; PD-L1; CTLA-4

Bispecific antibodies are engineered antibodies where the multiple specificities are joined together within the same molecules. They serve a variety of biological functions including, for example, T cell recruitment, delivery of CAR-T cells, targeting toxin to tumor, activating T cells, blockade of receptors essential for tumor growth, activating monocytes for tumoricidal activity, re-targeting T cells to tumor, delivering chemotherapeutics to local tumors, enabling radioimmunotherapy and the like.

There are 2 major structural format categories: IgG-like formats and non-IgG-like formats. IgG-like formats: Quadroma, Knob-into-holes Dual variable domains Ig IgG-single-chain Fv (scFv), Two-in-one Fab (or Dual action Fab), Half molecule exchange, Kλ-bodies; Non-IgG-like formats: scFv based BsAbs, Nanobodies, Dock and lock methods, Dual affinity retargeting molecules (DARTs).

The following are non-limiting examples of bispecific antibodies:

CD8×CD19; anti-DLL4×anti-VEGF; anti-CD3×anti-EGFR; anti-CD3×anti-GD2; anti-CD3×anti-CD19; anti-CD3×anti-CD20; anti-CD3×anti-EpCAM; anti-CD3×anti-CEA; anti-CD3×anti-CD123; anti-CD3× anti-GPA33; anti-CD3×anti-HER2; anti-CD3×gp100; anti-CD3×anti-PSMA; anti-CD30×anti-CD16A; anti-CEA×di-DTPA-131I; anti-CEA×HSG; anti-CD3×anti-CD33; anti-angiopoietin 2×anti-VEGF-A; anti-Her-1× anti-Her-3; anti-Her2×anti-Her3; anti-IGF1R×anti-Her3; anti-Her1×anti-cMET; anti-CD64×anti-EGFR; B-cell maturation antigen (BCMA); anti-CD19×anti-CD22; anti-CD28×HMV-MAA; anti-CD32B×anti CD79B; nanoparticles; anti-EGFR×anti EDV; and radioimmunotherapy.

Compounds of Formula 1 may be conjugated, admixed with, or used in rapid succession in any of a number of cytotoxic agents, especially those that induces immunogenic cell death, or usage at metronomic doses that leads to immune stimulation. Non-limiting examples of cytotoxic agents include:

Acetic acid, ethanol, anthracyclines, anti-EGFR mAb 7A7, BK channel agonists, bortezomib, bortezomib plus mitomycin C plus hTert-Ad, cardiac glycosides plus non-ICD inducers, cyclophosphamide, GADD34/PP1, inhibitors plus mitomycin, Irradiation, LV-tS-MAC, measles virus, oxaliplatin, PDT with hypericin, thapsigargin plus cisplatin, doxorubicin, paclitaxel, oncolytic peptide LTX-315, Mitoxantrone, oxaliplatin, UVA irradiation, gamma radiation, Shikonin, EGFR-specific antibody 7A7, coxsackievirus B3

Compounds of Formula 1 may be conjugated, admixed with, or used in rapid succession in any of a number of agents that reduces systemic or local immunosuppression in cancer patients, which can be achieved by biologics like monoclonal antibodies, bispecific antibodies or small molecule chemical therapeutics. Immunosuppressive agents include the following non-limiting examples: (as defined above, the "target" is followed by examples of immunosuppressive agent):

T-regulatory cells T-regs: metronomic doses of cyclophosphamide, dendritic cell vaccine with daclizumab, the anti-CD25 monoclonal antibody, Tyrosine kinase inhibitors sorafenib, sunitinib and imatinib.

Myeloid derived suppressor cells MDSCs: fluorouracil and gemcitabine, DS-8273a, agonist antibody targeting the TRAIL R2 receptor (DR-5).

Compounds of Formula 1 may be conjugated, admixed with, or used in rapid succession in any of a number of DAMPs Damage associated molecular patterns, most of which are induced by during immunogenic cell death caused by different agents. Non-limiting examples of DAMPs and their receptors include (the DAMP is followed by its receptors):

ATP: P2Y2 and P2X7; BCL-2: TLR2; Calreticulin: CD91; Cyclophilin A: CD147; F-actin: DNGR1; HSP70, HSP90, HSP60, HSP72, GRP78 and GP96: CD91, TLR2, TLR4, SREC1 and FEEL1; Hepatoma-derived growth factor: Unknown receptor; Histones: TLR9; HMGB1: TLR2, TLR4, RAGE and TIM3; HMGN1: TLR4; IL-1α: IL-1R; IL-33: ST2; IL-6: IL-6R and GP130; Mitochondrial DNA: TLR9; Mitochondrial transcription factor A: RAGE and TLR9; Monosodium urate: Unknown; N-formyl peptides: FPR1; Reactive carbonyls and oxidation-specific epitopes: CD36, SRA, TLR2, TLR4 and CD14; Ribonucleoproteins, mRNA and genomic DNA: TLR3 S100A8, S100A9 and S100A12: RAGE Desired Physiochemical Properties Conventionally produced GC products, when dispersed, suspended or dissolved in aqueous solutions are very difficult to sterile filter and produce according to GMP standards. Indeed, as is known in the art, autoclaving and gamma sterilization will both degrade or somehow alter the structure of the final product.

Certain aspects described herein overcome the long unmet needs for improved therapeutic GC products by providing improved GCs that are not subject to the disadvantages of conventional approaches.

Manufacturing and Filtration

We demonstrated that sterilization by sterile filtration of GCs with $M_W$ values below 420 kDa is filterable, whereas higher molecular weights are not. Moreover, conventional GCs, as described in the prior art, including, for example PCT application no. PCT/US13/021903, were shown to be very difficult to sterile filter through a 0.22 μm sterile filter, which renders it unsuitable for commercial cGMP manufacturing. In contrast, the GC of Formula 1, which was discovered to have nonobvious rheological properties, was shown to be highly suitable for sterile filtration, cGMP manufacturing, and human use.

Diafiltration and Ultrafiltration are industry-standard methods for the purification and concentration, respectively, of polymer solutions. It has been surprisingly found that diafiltration and ultrafiltration is unexpectedly improved using the improved GCs of Formula 1 described herein. Conventional GCs were difficult to diafilter and ultrafilter, causing the filter to clog or otherwise fail, thus rendering it unsuitable for commercial cGMP manufacturing. The improved GC, on the other hand, was highly suitable for diafiltration and ultrafiltration, thus significantly improving the manufacturing process.

According to one example, a preparation is formulated as an aqueous solution possessing a pH from between about 5 to about 7.

A preparation can also be formulated as an aqueous solution comprising a buffered physiological saline solution consisting essentially of GC.

A preparation can also be formulated consisting essentially of GC polymer, wherein the GC polymer possesses up to, but not including, thirty (30) percent glycation.

According to a specific example, the glycated amino groups are present less than twenty nine percent of the total monomers. According to another example, the GC polymer includes glycated amino groups present from 1% to 8% of the total monomers. In yet another example, the GC polymer includes glycated amino groups present from 3 to 6% of the total monomers. In still another example, the GC polymer includes glycated amino groups present from about 0.5% to about 9.5% of the total monomers.

In another example, a preparation can be formulated consisting essentially of GC polymer, wherein the GC polymer possesses a degree of glycation (DG) of about five (5) percent of its total monomers.

In another example, a preparation can be formulated consisting essentially of GC polymer, wherein the GC polymer has a $M_W$ value is less than 420 kDa.

Another example includes a GC comprising about one (1) percent by weight of a GC polymer dispersed in an aqueous solution, said aqueous solution having a viscosity of between about one (1) centistoke to about one hundred (100) centistokes measured at about 25 degrees Celsius.

Yet another example includes an aqueous solution having about one percent by weight of GC and degree of glycation (DG) of less than twenty-nine (29) percent of said GC, wherein the aqueous solution has a viscosity from about one (1) centistoke to approximately one hundred (100) centistokes.

In yet another example, a preparation can be formulated consisting essentially of GC polymer, comprising about or above one percent by weight of the GC polymer dispersed in an aqueous solution, wherein the GC polymer possesses about five (5) percent glycation of its total monomers, and wherein the aqueous solution has a viscosity suitable for ease of injectability and administration to a subject.

In yet another example, a preparation can be formulated consisting essentially of GC polymer, additionally containing one or more different materials miscible in an aqueous solution. Examples of suitable materials include, but are not limited to, hyaluronic acid, chondroitin sulfate and carboxymethylcellulose.

The preparation can include GC polymer comprising a monosaccharide bonded to an otherwise free amino group. The GC polymer can take any suitable form, such as a Schiff base, an Amadori product or mixtures thereof. The GC polymer can also be in the form of a reduced Schiff base (secondary amine), a reduced Amadori product (alcohol) or mixtures thereof.

The preparation can also be formulated wherein the GC polymer possesses a number of chemically modified monosaccharide or oligosaccharide substituents. In one example, the monosaccharide comprises galactose.

The formulations or preparations also contain GC in a physiologically compatible carrier.

The above and other objects are presently realized, certain aspects of which relate to GCs having particular chemical structure and composition that confer unexpected and surprisingly beneficial properties.

The present invention also encompasses a wide range of uses of GCs that have surprising and unexpected properties as immune stimulants, for instance in connection with tumor ablation, radiation therapy, cytotoxic agents, checkpoint inhibitors such as anti-PD-1 and PD-L1 antibodies, adoptive immunity transfer, cytokine therapy, and other therapeutic applications as described further herein.

In certain aspects described herein provide immune stimulants comprising an injectable GC preparation. Desirably, our GCs with a $M_W$ of less than 420 kDa are used for other therapeutic applications, including therapeutic use as an adjunct to tumor ablation or radiation therapy, or other therapies that may induce immunogenic cell death of tumor cells, and as an immune stimulant and immunomodulator in association with immunological therapies.

Modes of Administration

The discovery also encompasses various routes of administering the GC immune stimulant formulations, such as via intramuscular injection, subcutaneous injection, intradermal injection and intratumoral injection. In a desired approach, the immune stimulant is in one example prepared as a formulation for injection into or around the tumor mass. It should be recognized however that other methods may be sufficient for localizing the immune stimulant in the tumor site. One such alternative delivery means is conjugation of the immune stimulant to a tissue specific antibody or tissue specific antigen, such that delivery to the tumor site is enhanced. Any one method, or a combination of varying methods, of localizing the immune stimulant in the tumor site is acceptable so long as the delivery mechanism insures sufficient concentration of the immune stimulant in or around the neoplasm.

For certain lung cancers, nebulization is contemplated in which a desired amount of the GC of Formula 1 is administered locally through updraft to one or both lungs.

According to certain aspects, the discovery provides for various pharmaceutical formulations comprising GC used in connection with tumor ablation, including thermal tumor ablation such as radiofrequency ablation (RFA), photothermal laser ablation (PTT), high-intensity focused ultrasound (HIFU), and microwave ablation (MWA); non-thermal ablation such as irreversible electroporation (IRE), electric field therapy, photodynamic cancer therapy (PDT), and cryoablation; and tumor radiation therapy such as stereotactic body radiation therapy (SBRT), photon beam or proton beam therapy, and flash radiation therapy; and/or other tumor destruction methods, as described in further detail herein. It has been observed that it is desirable to utilize GCs having a suitable viscosity that enables their use as an injectable or other formulation as an adjunct to methods that induce immunogenic cell death of neoplasms, such as tumor ablation methods, tumor radiation methods, and/or other methods, including but not limited to chemotherapy and/or tumor immunotherapy methods. Such applications typically involve injection of the GC formulation into the corpus of a patient although other routes of administration are within the contemplation of inventors (e.g. inhalation).

The immune stimulant composition can further include an antitumor antibody conjugated to the GC. The immune stimulant composition can also include one or more tumor specific antigens conjugated to, or admixed with, the GC.

The immune stimulant composition can further include cytokines, chemokines, or (target toll-like receptor) TLR agonists, vaccine adjuvants, tumor-associated antigens, anti-tumor antibodies, DAMPs that are conjugated to, or admixed with, the GC.

The discovery provides an immune stimulant formulation that includes a suspension or a solution of GC. The GC is in this example used in connection with local ablation of a neoplasm using thermal or non-thermal ablation methods such as RFA, microwave, laser, HIFU, IRE, PDT, and cryoablation.

The GC is used in connection with radiation treatment of a neoplasm, such as SBRT or proton beam therapy.

As described in further detail herein, the immune stimulant formulations can further include a suitable chromophore for photodynamic or photothermal therapy. The selection of an appropriate chromophore is largely a matter of coordination with an acceptable laser wavelength of radiation. The wavelength of radiation used must, of course, be complementary to the photoproperties (i.e., absorption peak) of the chromophore. Other chromophore selection criteria include ability to create thermal energy, to evolve singlet oxygen and other active molecules, or to be toxic in their own right such as cisplatin. In one example a wavelength of radiation is 805.+/−0.10 nm. The desired chromophores have strong absorption in the red and near-infrared spectral region for which tissue is relatively transparent. Another advantage of this wavelength is that the potential mutagenic effects encountered with UV-excited sensitizers are avoided. Nevertheless, wavelengths of between 150 and 2000 nm may prove effective in individual cases. Examples of chromophores include, but are not limited to, single walled carbon nanotubes (SWNT), buckminsterfullerenes ($C_{60}$), indocyanine green, methylene blue, gold nano rods, DHE (polyhaematoporphrin ester/ether), mm-THPP (tetra(meta-hydroxyphenyl)porphyrin), $AlPcS_4$ (aluminum phthalocyanine tetrasulphonate), $ZnET_2$ (zinc aetio-purpurin), and Bchla (bacterio-chlorophyll-α).

Various Treatment Protocols are Contemplated Including the Following Twenty-Seven (27) Example Paragraphs:

1. In one example, the immune stimulant composition is formulated as a solution or suspension. The solution or suspension can include, for instance, about 1% by weight of GC
2. In another example, a composition for conditioning a neoplasm using tandem ablation therapy, for example by using physical methods such as heating or freezing the neoplasm, and immunological treatment, comprising an immune stimulant, wherein the immune stimulant is conjugated to a tumor specific antigen, and wherein the immune stimulant is GC.
3. In one example, a composition for conditioning a neoplasm using tandem ablation therapy, for example by means of physical methods such as heating or freezing the neoplasm, and immunological treatment, comprising an immune stimulant, wherein the immune stimulant is conjugated to a cytokine, and wherein the immune stimulant is GC.
4. In another example, a composition for conditioning a neoplasm using tandem ablation therapy, for example by means of physical methods such as heating or freezing the neoplasm, and immunological treatment, comprising an immune stimulant, wherein the immune stimulant is conjugated to a TLR agonist, and wherein the immune stimulant is GC.
5. In another example, a composition for conditioning a neoplasm using tandem radiation therapy, for example by means of X-rays, gamma rays, or proton beams, and immunological treatment, comprising an immune stimulant, wherein the immune stimulant is conjugated to a tumor specific antigen, and wherein the immune stimulant is GC.
6. In another example, a composition for conditioning a neoplasm using tandem radiation therapy, for example by means of X-rays, gamma rays, or proton beam, and immunological treatment, comprising an immune stimulant, wherein the immune stimulant is conjugated to a cytokine, and wherein the immune stimulant is GC.
7. In yet another example, a composition for conditioning a neoplasm using tandem radiation therapy, for example by means of X-rays, gamma rays, or proton beam, and immunological treatment, comprising an immune stimulant, wherein the immune stimulant is conjugated to a TLR agonist, and wherein the immune stimulant is GC.
8. In another example, a composition for conditioning a neoplasm using tandem physical and immunological treatment, comprising an immune stimulant, wherein the immune stimulant is conjugated to an antigen specific antibody and a cytokine, and wherein the immune stimulant is GC. The immune stimulant can, in certain instances, consist essentially of GC.
9. In one example, a composition for conditioning a neoplasm using tandem cytotoxic therapy, and immunological treatment, comprising an immune stimulant, wherein the immune stimulant is conjugated to a tumor specific antigen, and wherein the immune stimulant is GC.
10. In one example, a composition for conditioning a neoplasm using tandem cytotoxic therapy and immunological treatment, comprising an immune stimulant, wherein the immune stimulant is conjugated to a cytokine, and wherein the immune stimulant is GC.
11. In one example, a composition for conditioning a neoplasm using tandem cytotoxic therapy and immunological treatment, comprising an immune stimulant, wherein the immune stimulant is conjugated to a TLR agonist, and wherein the immune stimulant is GC.
12. In one example, a composition for conditioning a neoplasm using tandem physical and immunological treatment, comprising a combination of a chromophore and an immune stimulant, wherein the chromophore and the immune stimulant are conjugated to a tumor specific antibody, and wherein the immune stimulant is GC. The immune stimulant can, in certain instances, consist essentially of GC.

13. In one example, there is provided injectable formulations for conditioning a neoplasm using physical methods such as tumor ablation or radiation therapy, or cytotoxic therapy, or any combination thereof, in conjunction with immunological treatment, comprising of an immune stimulant, wherein the immune stimulant is GC. The immune stimulant, may in certain cases be conjugated to another component, such as, but not limited to, a cytokine, a chemokine, a TLR agonist, an antibody, a tumor-specific antigen, or any combination thereof.
14. A composition may furthermore be prepared for conditioning a neoplasm for tandem physical treatment, such as tumor ablation or radiation therapy, and immunological treatment, comprising an immune stimulant, and wherein the immune stimulant is GC with $M_W$ of less than 420 kDa.
15. A composition may also be prepared for use in conditioning a neoplasm for tandem physical treatment, such as tumor ablation or radiation therapy, and immunological treatment, comprising a combination of an immune stimulant and a cytokine, and wherein the immune stimulant is GC with a $M_W$ of less than 420 kDa.
16. Furthermore, an injectable solution may be prepared for conditioning a neoplasm for tandem physical treatment, such as tumor ablation or radiation therapy, and immunological treatment comprising an immune stimulant wherein the immune stimulant is GC with a $M_W$ of less than 420 kDa.
17. An injectable solution may also be prepared for conditioning a neoplasm for tandem physical treatment, such as tumor ablation or radiation therapy, and immunological treatment comprising a mixture of cytokine or TLR agonist and an immune stimulant wherein the immune stimulant is GC with a $M_W$ of less than 420 kDa.
18. In one example, the GC compositions is used as an immune stimulant in a novel cancer treatment. Physical and immunological therapies are combined by ablating or irradiating the neoplasm directly, and subsequently introducing the immune stimulant into or around the ablated or irradiated neoplasm. Following the administration of tumor ablation or irradiation sufficient to induce neoplastic cellular destruction, immune responses to the tumor associated antigens thus released are enhanced by the immune stimulant component by enhancing retention and exposure of tumor antigen, enhancing uptake of tumor antigen by antigen-presenting cells (APCs) such as dendritic cells (DCs), and by activating the APCs to avoid tolerance, and ultimately stimulate a systemic anti-tumor T cell response, wherein the immune stimulant is GC with a $M_W$ of less than 420 kDa.
19. In another example, photodynamic and immunological therapies are combined by introducing both a chromophore and an immune stimulant into a neoplasm, wherein the immune stimulant is GC. Upon application of a laser with irradiance sufficient to induce neoplastic cellular destruction, immune responses to the tumor associated antigens thus released are enhanced by the immune stimulant component by enhancing retention and exposure of tumor antigen, enhancing uptake of tumor antigen by APC such as DCs, and by activating the APC to avoid tolerance, and ultimately stimulating a systemic anti-tumor T cell response.
20. The immune stimulant may be combined with other components, such as cytokines, chemokines, TLR agonists, cytotoxic compositions, antibodies, or antigens, into a solution for injection into the tumor mass, or they may be injected separately into the tumor mass. It should be recognized however that other methods may be sufficient for localizing the immune stimulant in the tumor site. One such alternative delivery means is conjugation of the immune stimulant to a tissue-specific antibody or tissue-specific antigen, such that delivery to the tumor site is enhanced. Any one method, or a combination of varying methods, of localizing the immune stimulant in the tumor site is acceptable so long as the delivery mechanism ensures sufficient concentration of the immune stimulant in the neoplasm.
21. According to another example, a method for treating a neoplasm in a human or other animal host, comprises: (a) selecting an immune stimulant, wherein the immune stimulant comprises GC; (b) ablating or irradiating a selected neoplasm whereby neoplastic cellular destruction and immunogenic cell death of the neoplasm is induced, producing fragmented neoplastic tissue and cellular molecules; and (c) introducing the immune stimulant into or around the neoplasm, wherein the immune stimulant is GC, which stimulates the self-immunological defense system of the host to process the fragmented neoplastic tissue and cellular molecules, such as tumor antigens, and thus creates an immunity against neoplastic cellular multiplication.
22. In yet another example, a method of producing tumor-specific antibodies in a tumor-bearing host, includes ablating or irradiating a tumor to a degree sufficient to induce neoplastic cellular destruction and generating fragmented neoplastic tissue and cellular molecules, followed by the introduction of an immune stimulant into or around a neoplasm by means of injection wherein the immune stimulant is GC. The host's immune system is stimulated to interact with and process fragmented neoplastic tissue and cellular molecules, upon which a systemic anti-tumor antibody/B cell response is induced.
23. In another example, a method of producing tumor-specific T cells in a tumor-bearing host, includes ablating or irradiating a tumor to a degree sufficient to induce neoplastic cellular destruction and generating fragmented neoplastic tissue and cellular molecules, followed by the introduction of an immune stimulant into or around a neoplasm by means of injection, wherein the immune stimulant is GC, so that the host's immune system is stimulated to interact with and process fragmenteda neoplastic tissue and cellular molecules, upon which a systemic anti-tumor T cell response is induced.
24. An exemplary method of destroying a neoplasm and concurrently generating an anti-tumor T cell response in a tumor-bearing host, includes: (a) selecting an immune stimulant; (b) ablating or irradiating the neoplasm sufficient to produce a neoplastic cellular destruction and generating fragmented neoplastic tissue and cellular molecules; (c) introducing the immune stimulant into the neoplasm by intratumoral injection, wherein an amalgam of the fragmented tissue and cellular molecules and the immune stimulant is formed at the injection site; and (d) stimulating a T cell response against neoplastic cellular tissue within the host.

25. Another exemplary method of destroying a neoplasm and concurrently generating an anti-tumor T cell response in a tumor-bearing host, includes: (a) selecting a chromophore and an immune stimulant, the chromophore being suitable to generate thermal energy upon activation in the near-infrared or infrared wavelength range; (b) introducing the chromophore into the neoplasm by intratumor injection; (c) irradiating the neoplasm with a laser of a wavelength in the visible, near-infrared or infrared range, at a power and for a duration sufficient to activate the chromophore to produce a photothermal reaction inducing neoplastic cellular destruction and generating fragmented neoplastic tissue and cellular molecules; (d) introducing the immune stimulant into the neoplasm by intratumoral injection, wherein the immune stimulant is GC, where an amalgam of the fragmented tissue and cellular molecules and the immune stimulant is formed; and (e) stimulating an anti-tumor immunological response systemically within the host.

26. As described elsewhere herein, the method can further include conjugating the immune stimulant to a tumor specific antibody, thereby forming a conjugate, and administering the conjugate to the host. Alternatively, the method can further include conjugating the immune stimulant to a tumor specific antigen, thereby forming a conjugate, and administering the conjugate to the host. Furthermore, any number of suitable conjugations can be used, for instance, cytokines, chemokines, TLR agonists, proteins, cytotoxic agents, or any combination thereof.

27. The preparations and formulations described herein, including the GCs, can also be used in conjunction with photodynamic therapy (PDT). Photosensitizing compounds show a photochemical reaction when exposed to light. Photodynamic therapy (PDT) uses such photosensitizing compounds and lasers to produce tumor necrosis. Treatment of solid tumors by PDT usually involves the systemic administration of tumor localizing, photosensitizing compounds and their subsequent activation by laser. Upon absorbing light of the appropriate wavelength, the sensitizer is converted from a stable atomic structure to an excited state. Cytotoxicity and eventual tumor destruction are mediated by the interaction between the sensitizer and molecular oxygen within the treated tissue to generate cytotoxic singlet oxygen.

Numerous Combinations of the Above Noted Paragraphs are Contemplated as Follows:

For compounds of Formula 1, tandem ablation therapy, for example, by using physical methods such as heating or freezing the neoplasm can include protocols (from paragraphs 2, 3, 4 and 13 above); tandem ablation therapy for example by means of X-rays, gamma radiation, or proton beam from (paragraphs 5, 6, 7, 8 and 13 above); for tandem cytotoxic therapy (from paragraphs 9, 10, 11 and 13 above); and tandem physical and immunological treatment comprising a combination of a chromophore and an immune stimulant (from paragraph 12 above)

For compounds of Formula 1 with Molecular Weights of less than 420 kDa, tandem ablation therapy, for example, by using physical methods such as heating or freezing the neoplasm can include protocols (from paragraphs 14, 15, and 17 above); tandem ablation therapy for example by means of X-rays, gamma radiation, or proton beam from (from paragraphs 14, 15, and 17 above).

For chromophores for PDT, by using tandem physical and immunological treatment comprising a combination of a chromophore and an immune stimulant (from paragraph 12 above)

For tumor antigens, tandem ablation therapy, for example by using physical methods such as heating or freezing the neoplasm, can include protocols (from paragraphs 2 and 13 above); tandem ablation therapy for example by means of X-rays, gamma radiation, or proton beam from (paragraphs 5 and 13 above); and for tandem cytotoxic therapy (from paragraphs 9 and 13 above).

For cytokines, tandem ablation therapy, for example by using physical methods such as heating or freezing the neoplasm, can include protocols (from paragraphs 3, 13, 15 and 17 above); tandem ablation therapy, for example by means of X-rays, gamma radiation, or proton beam from (paragraphs 6, 8, 13, 14, 15 and 17 above); and for tandem cytotoxic therapy (from paragraphs 10 and 13 above).

For chemokines, tandem ablation therapy, for example by using physical methods such as heating or freezing the neoplasm, can include protocols (from paragraph 13 above); tandem ablation therapy for example by means of X-rays, gamma radiation, or proton beam from (paragraph 13 above); and for tandem cytotoxic therapy (from paragraph 13 above).

For TLR agonist, tandem ablation therapy, for example by using physical methods such as heating or freezing the neoplasm, can include protocols (from paragraphs 4 and 13 above); tandem ablation therapy for example by means of X-rays, gamma radiation, or proton beams from (paragraphs 7 and 13 above); and for tandem cytotoxic therapy (from paragraphs 11 and 13 above).

For antibodies, tandem ablation therapy, for example by using physical methods such as heating or freezing the neoplasm, can include protocols (from paragraph 13 above); tandem ablation therapy for example by means of X-rays, gamma radiation, or proton beams from (paragraphs 8 and 13 above); for tandem cytotoxic therapy (from paragraph 13 above); and tandem physical and immunological treatment comprising a combination of a chromophore and an immune stimulant (from paragraph 12 above)

Cancer Treatment by Local Tumor Destruction in Combination with an Immune Stimulant It is desirable to utilize GCs having a suitable viscosity as injectable materials for use in the treatment of cancer. This can be achieved in any suitable manner, for instance, in conjunction with applications such as combined local tumor destruction methods, such as thermal or non-thermal tumor ablation, and tumor immunotherapy methods. The term cancer, as used herein, is a general term that is intended to include any of a number of various types of malignant neoplasms. They are cells derived from the body that have acquired at least 8 specific hallmarks through genetic and/or epigenetic mutations and/or other mechanisms: 1. Resisting cell death; 2. Sustaining proliferative signaling; 3. Evading growth suppressors; 4. Activation invasion and metastasis; 5. Enabling replicative immortality; 6. Inducing angiogenesis; 7. Avoiding immune destruction; and 8. Deregulating cellular energetics. Neoplasms are likely to recur after attempted removal or treatment and to cause death of the patient unless adequately treated.

Certain examples of cancers, such as carcinomas, sarcomas, and melanomas, that may be treated with GCs having a suitable viscosity as injectable materials include, but are not limited to, those of the liver, cervix, skin, breast, bladder, colon, rectal, prostate, larynx, endometrium, ovary, oral cavity, kidney, testis (non-semino-matous) and lung (non-small cell).

Moreover, treatment may also be administered in a suitable manner in conjunction with other types of cancer treatment, for instance, radiation treatment. Radiation plays a key role, for example, in the remediation of Hodgkin's disease, nodular and diffuse non-Hodgkin's lymphomas, squamous cell carcinoma of the head and neck, mediastinal germ-cell tumors, seminoma, prostate cancer, early stage breast cancer, early stage non-small cell lung cancer, and medulloblastoma. Radiation can also be used as palliative therapy in prostate cancer and breast cancer when bone metastases are present, in multiple myeloma advanced stage lung and esophagopharyngeal cancer, gastric cancer, and sarcomas, and in brain metastases. Cancers that may be treated include, for instance, Hodgkin's disease, early-stage non-Hodgkin's lymphomas, cancers of the testis (seminomal), prostate, larynx, cervix, and, to a lesser extent, cancers of the nasopharynx, nasal sinuses, breast, esophagus, and lung.

Treatment may also be administered in a suitable manner in conjunction with other types of antineoplastic drugs. Antineoplastic drugs include those that prevent cell division (mitosis), development, maturation, or spread of neoplastic cells. The ideal antineoplastic drug would destroy cancer cells without adverse effects or toxicities on normal cells, but no such drug exists. Certain stages of choriocarcinoma, Hodgkin's disease, diffuse large cell lymphoma, Burkitt's lymphoma and leukemia have been found to be susceptible to anti-neoplastics, as have been cancers of the testis (non-seminomatous) and lung (small cell cancer). Common classes of antineoplastic drugs include, but are not limited to, alkylating agents, antimetabolites, plant alkaloids, antibiotics, nitrosoureas, inorganic ions, enzymes, and hormones.

Improving Outcomes of Tumor Ablation and Ablative Radiation Methods

The semi-synthetic biopolymer compositions described herein are thus useful in a myriad of applications, including, for instance, as an immune stimulant or as a component of an immune stimulant, as described in detail herein. Notwithstanding other uses, a principal use of the GC is as an immune stimulant in connection with physical destruction of tumors using common or standard-of-care tumor ablation methods, such as RFA, Microwave, HIFU, Laser, Cryoablation, IRE, and PDT, or ablative radiation methods, such as SBRT and proton beam, and it is in this context that the compounds of Formula 1 compositions are described in detail herein.

As described further herein, additional aspects are directed to uses of the compounds of Formula 1 preparations described herein as immune stimulants in conjunction with common tumor ablation or radiation therapy. Utilizing the present compositions in one example encompasses introducing into or around a neoplasm an immune stimulant comprising GC compositions before, during, or after tumor ablation or radiation treatment of the same tumor. The ablation or radiation treatment is performed in a way that is sufficient to induce neoplastic cellular destruction, and combined with injection of, or by other means delivered, the GCs of the present invention, a systemic anti-tumor immune response is induced.

In one aspect, compositions of Formula 1 are utilized in conjunction with surgical removal of neoplasms.

In certain other aspects, the outcomes of tumor ablation and radiation therapy are improved, wherein the improvement comprises the use of the herein-described injectable GCs of Formula 1. The present discovery also contemplates methods of activating specific components of the immune system in conjunction with a systemic anti-tumor immune response, comprising treatment with a GC.

As described further herein, it has been determined that administration of GCs described herein in conjunction with tumor ablation and radiation therapy overcomes limitations of current tumor ablation and radiation therapies. In general, the two underlying principles for the improvement are (1) reducing the recurrence rate at local tumor ablation or radiation therapy sites that devitalize a targeted tumor and liberate tumor antigens, and (2) localization of injection of an immune stimulant comprising of GC, which interacts with liberated tumor antigens, and activates antigen-presenting cells such as dendritic cells, to induce a systemic immune response against the cancer, also known as an "abscopal" effect. Thus, the GCs described herein effectively interact both with tumor antigens liberated from the ablated or radiated tumor cells or remnants of tumors following surgery, and with certain components of the immune system, such as dendritic cells, macrophages, neutrophils and other tumor infiltrating myeloid and lymphoid cells.

Another advantage of using the herein-described injectable compounds of Formula 1 preparations, in conjunction with tumor ablation or radiation therapy, is the direct activation of dendritic cells (DCs) by the GC of the present invention, which is an important step to prevent tumor tolerance following exposure to tumor antigen.

Compounds of Formula 1 where the $M_W$ is less than 420 kDa described herein also function to stimulate the immune system and induce antigen-specific immunity by 1) activating dendritic cells, 2) increasing the exposure of ablation-liberated tumor antigens and dendritic cells, and 3) increasing the tumor antigen uptake by the dendritic cells to initiate a systemic T cell response against the cancer.

Thus, in accordance with one example, formulations of GC activate one or more components of the immune system, mediating desired therapeutic effects.

The injectable GCs have unexpected utility to induce an abscopal effect following tumor ablation and radiation therapy, which, among other factors, is based on the activation of antigen-presenting cells (e.g., dendritic cells and macrophages), and the subsequent exposure of tumor antigens to the antigen-presenting cells.

Figure 8:
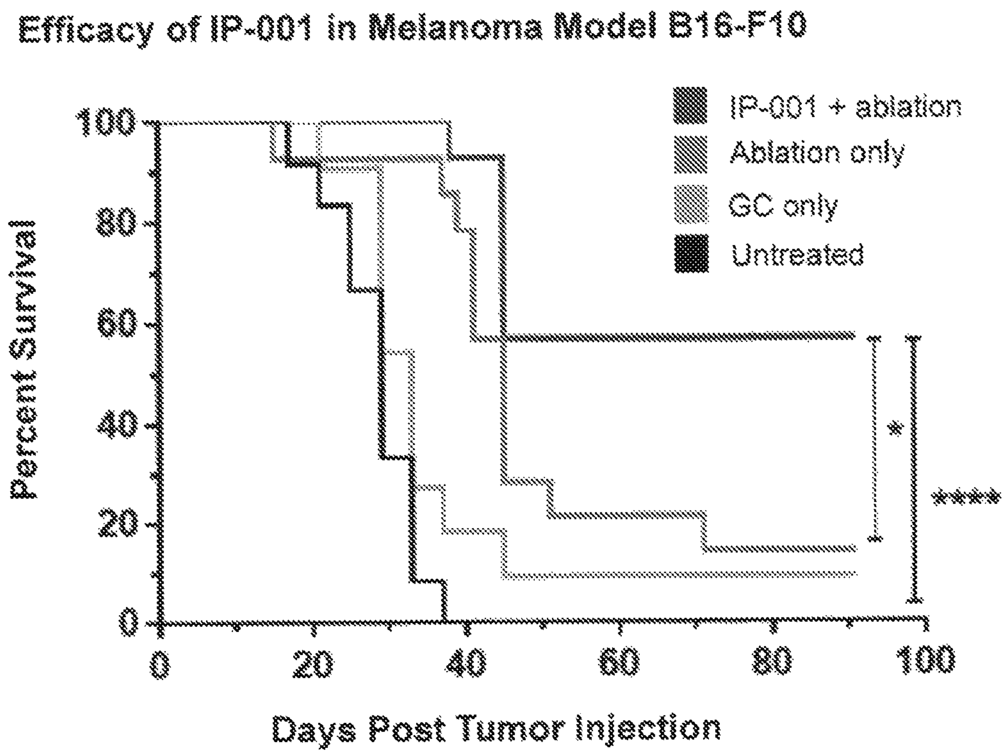
FIG. 8 is a graph showing the Efficacy of the Formula 1 compound when administered in conjunction with tumor ablation in a B16-F10 mouse melanoma tumor model double flank experiment.

In one experiment, this abscopal effect was demonstrated in a B16-F10 mouse melanoma model, where two tumors were implanted in a mouse, but only one tumor was treated with ablation in conjunction with GC of Formula 1 where the $M_W$ is less than 420 kDa. As seen in FIG. 8, because of the aggressive nature of B16-F10 melanoma tumors, any remaining tumor deposit will grow progressively and causes termination of the animals. Therefore, only when tumors on the opposite flank were eliminated due to an anti-tumor immune response, also known as an abscopal effect, could the animal survive long-term. All untreated animals reached their endpoint (tumor grown to the maximal tolerated size/death/terminal due to severe health decline) within 40 days as expected. While tumor ablation alone or GC alone did lead to minimal long-term survival at ~14% (GC alone at ~9%), the injection of GC of Formula 1 where the $M_W$ is less than 420 kDa after ablation significantly improved the efficacy, more than 3-fold, resulting in 57% long term survival.

Another advantage of using the herein-described injectable GCs of the present invention, in conjunction with tumor ablation or radiation therapy or other means of inducing immunogenic cell death, is that by using this approach, this method independently triggers the immune response in each individual, and does not depend upon the expression of same specific tumor-specific antigen(s) across recipient hosts (as is required in conventional antibody immunotherapy and vaccination). Animal research has revealed that in addition to improved long-term survival and elimination of both primary tumors and distant metastases, $CD4^+$ $IFN\gamma^+$ and $CD8^+$ $IFN\gamma^+$ T cells infiltrate distant untreated tumors (metastases) when GC is injected intratumorally in conjunction with tumor ablation of the primary tumor of the studies animals. Additionally, was also shown that successfully treated animals could acquire long-term resistance to tumor re-challenge, and combined with other data this further supports that a Th1 type immune response is induced.

Thus, using the injectable GCs described herein, there are several advantages that meet critical needs in providing effective cancer treatment. This is particularly advantageous for cancer patients, since the preparations described herein also provide surprisingly and unexpectedly beneficial preparations that are easy to administer by injection, and that fits well in the workflow in the clinic, and therefore provide effective adjunct treatment options to conventional tumor ablation and radiation therapies that are otherwise not effective against metastases, and that are sensitive to local recurrence if the tumor margins are not sufficiently treated. The injectable compounds of Formula 1, as described herein, provide several advantages that meet critical needs in providing effective cancer treatment.

The GCs described herein have been shown to induce maturation of dendritic cells (assessed by CD40 expression), enhance T-cell proliferation, increase $IFN\gamma$, $TNF\alpha$, and IL-12 secretion in serum and in re-stimulated splenocytes of tumor ablated animals. Furthermore, the combined effects of ablation (for instance, radiofrequency ablation and injection of GCs in accordance with the present invention) has been shown to induce tumor-specific immunity, with an infiltration of $CD4^+$ $IFN\gamma^+$ and $CD8^+$ $IFN\gamma^+$ T cells, as well as a reduction of regulatory T cells, in distant untreated metastases.

As described in further detail herein, injection of GCs described in conjunction with some method that induces immunogenic tumor cell death, such as tumor ablation or radiation therapy, thus provides numerous advantages over conventional tumor ablation and radiation therapies, including, but not limited to:

Enhances local outcomes of ablated or radiated tumors
Eliminates untreated metastases by inducing abscopal effect
Induces long-term immunity and survival
Reduces tumor recurrence
Has limited toxicity and is well-tolerated at therapeutic doses As described further herein, the preparations have several advantages over other conventional and unconventional treatment modalities. The combination of tumor destruction and injection of compounds of Formula 1 is the key. The most significant advantage is that compounds of Formula 1 effectively transforms a local tumor ablation or radiation therapy into a systemic immunotherapy for cancer that is now capable of eliminating distant non-ablated or non-radiated metastases. Compounds of Formula 1 are thus capable of inducing a prominent abscopal effect of the otherwise local tumor ablation or radiation therapy. When local tumor destruction occurs following tumor ablation or radiation therapy, the fragmented tissue and cellular molecules are locally released within the host. In a normal circumstance, these cellular molecules, such as tumor antigens, are quickly cleared from the treated area by normal physiological mechanisms, which means that when antigen-presenting cells (APC) enter the area over the next several days following the ablation event, their exposure to tumor antigen is limited, and this contributes to only inducing a limited downstream T cell response. However, when a compound of Formula 1 is injected into the tumor after tumor ablation, the compounds of Formula 1 will interact with and localize these tumor antigens due to its unique electrostatic and physiochemical properties, effectively increasing the exposure of tumor antigen to infiltrating APC. Furthermore, in a critical step, compounds of Formula 1 activate the dendritic cells, as measured by for example CD40 expression, which is a crucial step in order to induce a systemic anti-tumor immune response against the ablated cancer.

In summary, long-term survival with total cancer eradication can be achieved by using compounds of Formula 1. It is a combined result of reduced tumor burden due to local tumor elimination, for example by tumor ablation, and an enhanced immune system response due to the interaction between tumor antigens and compounds of Formula 1, and the direct activation of dendritic cells by compounds of Formula 1 as described in further detail herein.

Further examples are provided by way of illustration and are not intended in any way to limit the scope of the discovery. The examples should therefore not be construed as limitations on the scope of the discovery, but rather should be viewed as exemplifications of certain aspects thereof. Many other variations are possible.

Activation of Dendritic Cells

In one experiment, DCs were activated by compounds of Formula 1, manifested as upregulation of CD40, in a dose dependent manner as demonstrated previously. Conventional GC with molecular weights about 500 kDa or greater, on the other hand, did not affect DC activation as measured by CD40 expression. This represents a significant difference in in vitro function, which is a key link in initiating the downstream T cell response.

Without wishing to be bound by theory, we believe the main difference between conventional GC and compounds of Formula 1 lies in the $M_W$ (conventional GC has a molecular weight of about 500 kDa or greater, compounds of Formula 1 have a molecular weight of less than 420 kDa), and the method of sterilization. Any of such factors could contribute to the discrepancy in DC activation capability.

Assuming there are specific receptors for compounds of Formula 1, autoclaving procedure carries with it a high propensity to change the special orientation of the molecule and it no longer fits the pocket of the receptor on DCs. Another speculation is that within compounds of Formula 1, the optimal $M_W$ for activating DCs lies below the value of $M_W$ for the conventional GC.

In summary, we have demonstrated that compounds of Formula 1 activate DCs, indicated by increased expression of CD40. We, inventors, believe this is an important part of the mechanism of action in GCs anti-tumor properties. Conventional GC doesn't possess the same capability in our experimental system.

EXAMPLES

Example 1

Exemplary Process for the Preparation of GC

GC is obtained by reacting chitosan with a monosaccharide and/or oligosaccharide, in one example in the presence of an acidifying agent, for a time sufficient to accomplish Schiff base formation between the carbonyl group of the sugar and the primary amino groups of chitosan (also referred to herein as glycation of the amino group). This is followed by stabilization by reduction of Schiff bases and of their rearranged derivatives (Amadori products).

Example 2A

Sterile Filtration

While a conventional 1,500 kDa galactochitosan, described in U.S. Pat. No. 5,747,475, is reported to be readily synthesized, the sterilization with, for example, a 0.22-micron filter is impossible without compromising the integrity of the filter, thus rendering the conventional GC unsuitable for GMP production and human use. Moreover, conventional GC with a molecular weight of greater than 420 kDa, failed in our attempts at sterile filtration. In contrast, the formulation of the compounds of Formula 1, described herein has significant advantages with regard to GMP production and sterile filtration due to unexpected and beneficial chemical structure and composition. For example, at a $M_W$ of 250 kDa, sterile filtration with a 0.20-0.22 micrometer filter is highly feasible, with a steady flow rate without loss of material during filtration.

Example 2B

Demonstration of the Sterile Filterability of a Compound of Formula 1 in Example 2A Compounds of Formula 1 are an illustrative example of GC, which is a semi-synthetic glucosamine-based polymer. Compounds of Formula 1 are a novel and unobvious GC. Specifically, the data below supports the advantageous and unexpected properties of compounds of Formula 1 with respect to its ability to be manufactured in a consistent and compliant manner. The compounds of Formula 1 are formulated as a 1.0% solution (w/w) in water buffered to pH of 5-6 and has a viscosity of 50-60 cPs and is meant for intratumoral injection. Compounds of Formula 1 are a variant of GC and has the following molecular characteristics:

Weight Averaged Molecular Weight ($M_W$) of ~250 kDa
Degree of Deacetylation (DDA) of ~80%
Degree of Glycation (DG) of ~5%

One of the main advantages exhibited by compounds of Formula 1 are their ability to be sterile filtered, particularly those with $M_W$ of less than 420 kDa. The sterile filtration of pharmaceutical solutions is an industry standard for ensuring patient safety. Specifically, in the area of sterile injectable solutions, sterile filtration is often the favored method for sterilization, as it is an easily scalable process and does not affect the chemical structure of the active pharmaceutical ingredient (API) as often occurs during autoclave-based or gamma irradiation-based sterilizations. Additionally, sterile filtration offers cost advantages in the development, validation and execution of the process relative to autoclave and gamma sterilization. The sterile filtration of solutions of polymers adds an additional degree of complexity, as certain chemical structures and compositions can often slow or stop the filtration process. Therefore, the conditions of the filtration as well as the chemical and physiochemical characteristics of the polymer must be considered carefully.

With respect to compounds of Formula 1, it was unexpectedly discovered that the specific example in conjunction with a formulation including defined ranges of concentration and pH were needed to successfully sterile filter the formulation and provide a compliant and consistent drug product. As shown below, the results of our experiments demonstrate the filterability compared to aspects of GC that are outside of the exemplified ranges, described above and specifically include those with a molecular weight of less than 420 kDa.

Under current regulatory and scientific standards, pharmaceutical solutions can be considered sterile following the filtration through a filter with an effective pore-size of 0.22 microns or smaller. Additionally, the process and materials must be tested and validated in a GMP-compliant manner. The sterile filtration of compounds of Formula 1 drug product has been carefully studied. The full-scale process for the sterilization of compounds of Formula 1 utilize Pall Corporations Flurodyne 0.20 um capsule filters (part #KA2DFLP1S) in a redundant (serial) manner. The filter chosen meets all regulatory requirements and is chemically compatible with compounds of Formula 1. Additionally, a product-specific validation of the process (Study #-VAL-AM-000754-B) was carried out. As part of this study, solutions of Formula 1 demonstrated multiple times their ability to effectively undergo sterile filtration.

Referring to FIG. 2 (recirculation data for compounds of Formula 1 Drug Product), the data clearly shows that when solutions of Formula 1 are recirculated through sterilizing-grade membranes for up to 3 hours at a constant pressure there is minimal loss in flow rate (indicating minimal fowling or clogging of the filter). This test represents an extreme stressing of the system, as sterile filtration in practice is only a single through 1 or 2 filters and not a continuous recirculation of the solution through the membrane. This data strongly supports the fact that GC solutions with a molecular weight of less than 420 kDa can be filter sterilized with little to no loss in integrity of the polymer solution.

The process validated by Pall Corporation in Study VAL-AM-000754-B was subsequently performed on scale multiple time. In one example, the production of GMP-grade a solution of Formula 1, the following data was collected:

Pre-filtration weight of a compound of Formula 1 Drug Product—7.602 kg
Time for redundant sterile filtration—3 hours
Post-filtration weight of a compound of Formula 1 Drug Product—7.384 kg
Yield of filtration—97.1%

In order to demonstrate of the advantage of a compound of Formula 1 over other less desirable GC aspects with respect to sterile filtration, a direct comparison of sterile filtration of one of the certain aspects of Formula 1 and those with higher values of $M_W$ (>420 kDa) was performed.

A 1% solution of conventional GC with a $M_W$ of about 500 kDa was synthesized. Conventional GCs are sterilized by autoclave and we believe that this process would in fact affect the $M_W$ of the polymer. To test this, solutions of conventional GC were synthesized and autoclaved. The resulting GCs had $M_W$ values greater than 420 kDa and were tested for their abilities to be sterile filtered both before and after the reported autoclave sterilization and compared to that of examples of GCs reported herein.

Figure 3:
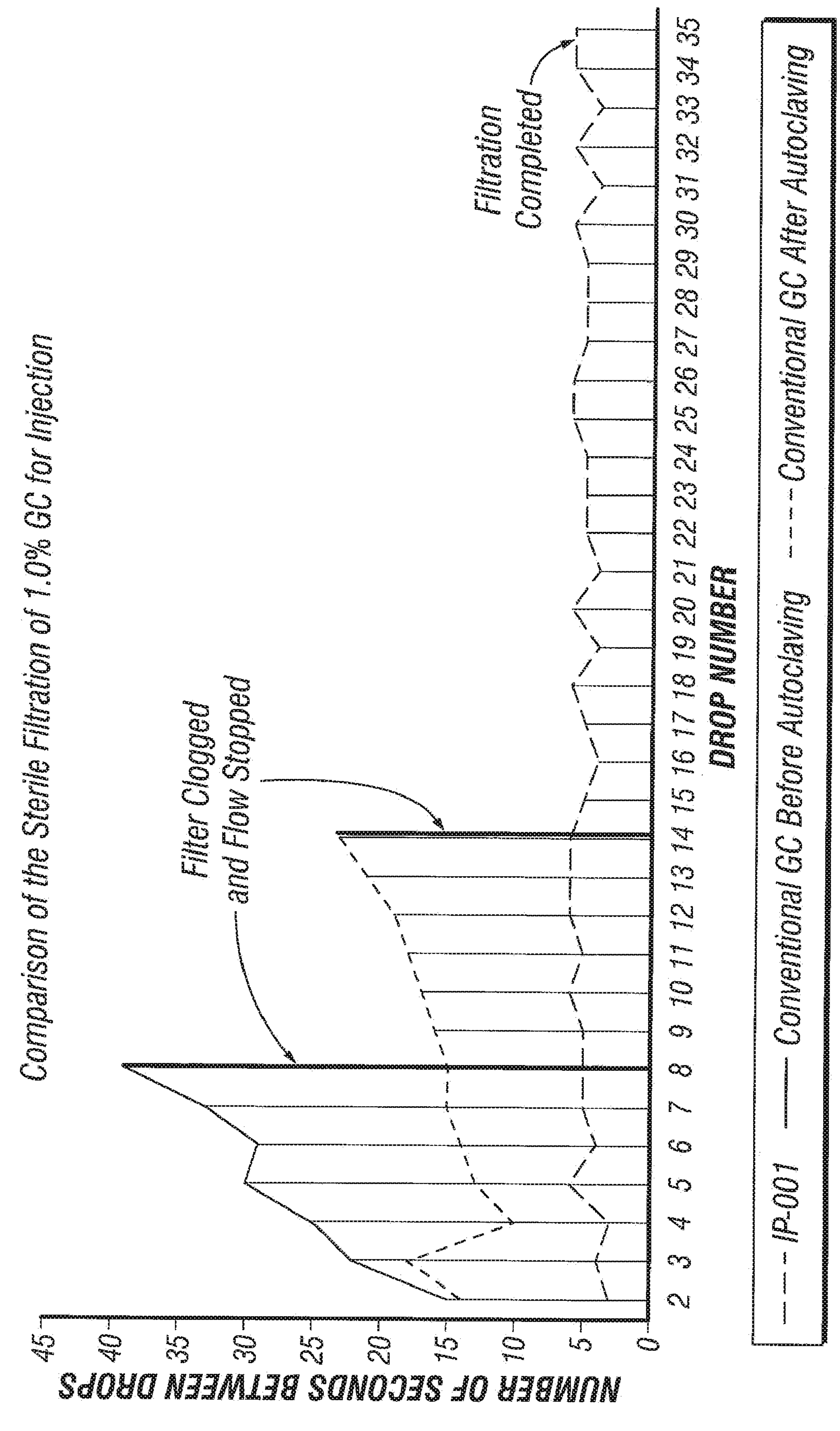
FIG. 3 is a graph showing comparative filtration rate data for various values of $M_W$ of 1% solutions of GC.

Referring now to FIG. 3, which shows filtration rate data for various 1% solutions of GC. In order to generate the data in FIG. 3, 1 mL of each solution was added to a 2.5 mL syringe fitted with a Luer-fitted digital pressure sensor. A small scale, representative sterilizing-grade filter with a Luer fitting was then attached to the outlet of the pressure sensor.

The solutions were forced through the filters keeping the pressure between 500 and 600 psi. The resulting flow rate was measured.

The data in FIG. 3 clearly shows that the compounds of Formula 1 with $M_W$ values lower than 420 kDa maintained a consistent flow rate until all the solution had been pushed through the filter. In contrast, the pre- and post-autoclave solutions of GCs with $M_W$ values of greater than 420 kDa GC exhibited steadily decreasing drop rates, both ultimately clogging the filters and thus halting the filtration. Additionally, the data supports that autoclaving solutions of GCs reduces the $M_W$, as shown by the lower pressures and improved flows for autoclaved materials when compared to non-autoclaved material.

Figure 4:
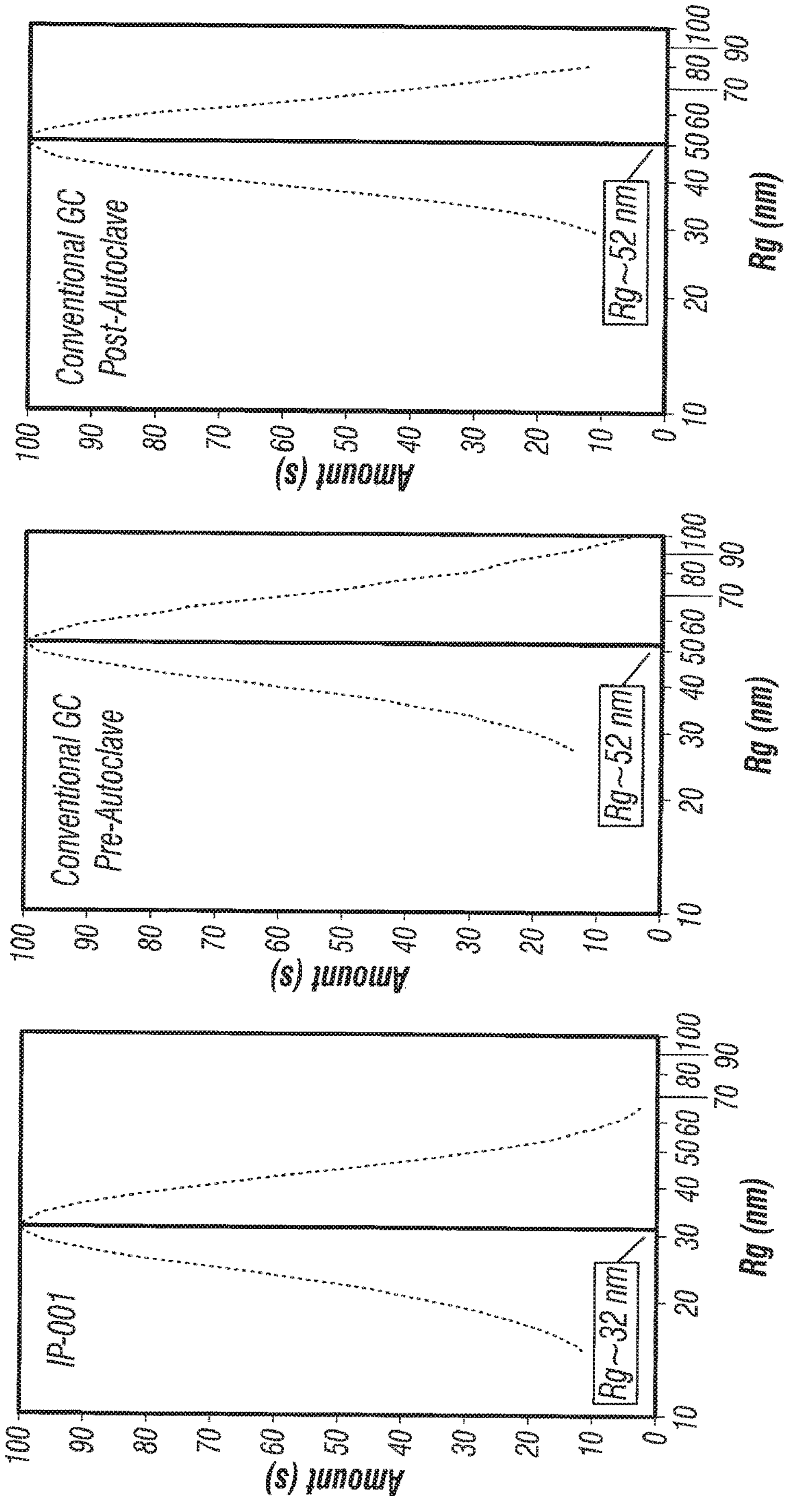
FIG. 4 illustrates particle size data for the three GC solutions in FIG. 3.

Referring now to FIG. 4, particle size data was collected for the 3 samples tested. A convenient estimate of particles sizes for chitosan solutions is the radius of gyration (Rg). While Rg is not the exact radius of the particle, more often than not, it is only slightly less than the actual radius of the particle. The radius of gyration for solutions of compounds of Formula 1 was measured to be ~32 nm while both GC solutions with $M_W$ values greater than 420 kDa GC exhibited Rg's of ~52 nm or higher. When the larger end of the polymer range is considered, we found that the conventional GC would not sterile filter, as the particles are apparently approaching or becoming larger than the effective pore size of the sterilizing filter.

The data described herein clearly demonstrates the advantage of the new and unobvious compounds of Formula 1 with respect to its sterile filterability when compared to conventional GC of molecular weights greater than 420 kDa. Additionally, and unexpectedly, compounds of Formula 1 represent an optimal form of GC for sterile filtration. It is known that lowering the pH of solutions of chitosan increases the Rg while increasing the pH of GC solutions causes the material to crash out of solution (i.e. precipitate). Therefore, it was unexpectedly discovered that one critical parameter for the sterile filtration of compounds of Formula 1 is the optimization of the pH, in contrast to conventional GC with molecular weights greater than 420 kDa which cannot be sterile filtered at any pH range. The data described herein and the additional development work performed for compounds of Formula 1 clearly support that the described example represents and clear and unexpected advantage when compared to conventional GCs.

Example 3

Improvement of Manufacturing

In this exemplary study, it was determined that experimental conditions could be adjusted as needed to improve overall yield during the manufacture of GC. It was unexpectedly discovered that manufacturing of GCs could be improved by controlling the pH conditions and provide better control of the percent glycation of the resulting GC. Specifically, it was determined that controlling the pH is critical in order to modulate the half-life of the active sodium borohydride ($NaBH_4$) in solution. The half-life of sodium borohydride is related to pH, with lower pH values significantly reducing the presence of active $NaBH_4$ through acid catalyzed decomposition of the reagent, resulting in lower values of DG. It was thus determined that $NaBH_4$ was not as effective in stabilizing the GC by reduction of the Schiff bases and Amidori products at lower pH. For instance, when the pH was kept below five (pH<5), the half-life of sodium borohydride is extremely short, and thus the reduction of the Schiff bases and Amadori products was less efficient, and percent glycation decreased.

Additionally, it was determined, that with higher pH values of the reaction mixture, formulation "gels" were observed due to the creation of a non-Newtonian solution. For instance, when the pH was kept above six (pH>6), the formulation was observed to gel. The gelling of the reaction lead to ineffective stirring and sodium borohydride dosing, thus halting the sodium borohydride reduction. In other words, to achieve the goal of efficiently manufacturing the GC solutions of Formula 1, the pH was optimized to provide a sufficient half-life of the sodium borohydride while maintaining conventional fluid characteristics of the solution.

Example 4

Use of Compositions of Formula 1 to Enhance Local Antigen Retention

Figure 12:
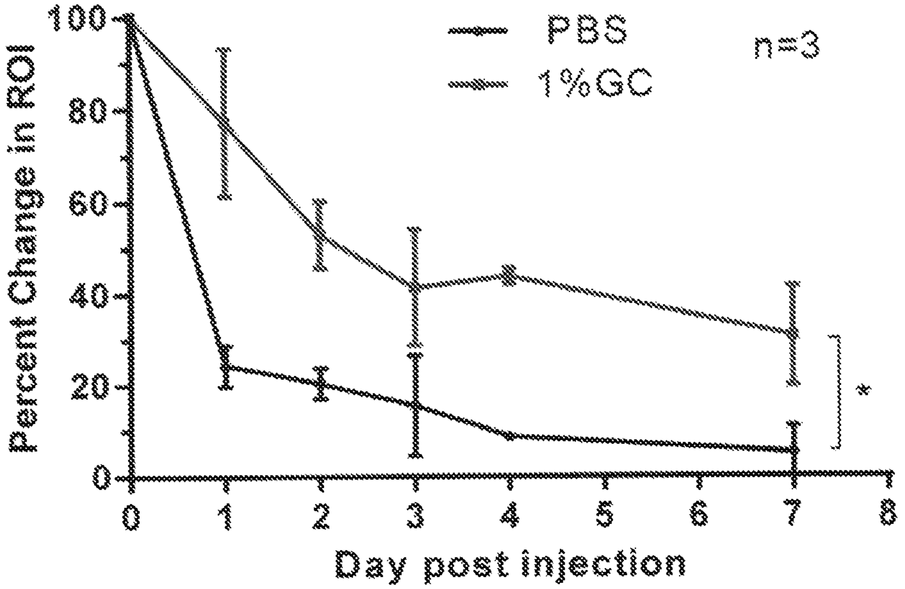
FIG. 12 is a graph showing the local retention of subcutaneously injected antigen OVA (labeled with Texas Red) in mouse.

Ablation-liberated tumor antigens are much more accessible for uptake by APCs compared to those inside intact tumor cells. This is the first step by which APCs initiate a downstream adaptive immunity against the tumor cells expressing these antigens. However, as discussed, a significant portion of these freshly liberated antigens will be lost and injection of a compound of Formula 1 preserves this critical information for the stimulation of the patient's immune system. To demonstrate such property, fluorescently labeled antigen OVA protein was injected subcutaneously after mixing with a compound of Formula 1 or PBS and the retention of the OVA was monitored by whole body imaging over 1 week. FIG. 12 shows that in the presence of a compound of Formula 1, local OVA concentrations were three- to four-fold higher than control animals within the first day of injection. The local antigen concentration declined over time but was maintained at a two- to three-fold higher level by a compound of Formula 1 for up to seven days. As such, a compound of Formula 1 prolongs the availability of tumor antigens for incoming APCs. This maximizes the chance for the immune system to acquire these antigens because although there are resident DCs (e.g. Langerhans cells/dermal DCs) at the treatment site, influx of APCs and monocytes, which differentiate into tissue DCs/MACs, can continue for days. In other words, the compound of Formula 1 increases the abundance of tumor antigens for the waves of APCs that arrive later.

Example 5

Use of Compositions of Formula 1 to Enhance the Efficacy of Tumor Ablation

To further verify the abscopal effect of ablation+a compound of Formula 1, we performed a double flank tumor injection experiment in another aggressive metastatic tumor model, B16-F10 melanoma in mouse. In this experiment, $2*10^5$ B16-F10 tumor cells were implanted on the right flank of C57BL/6 wildtype mice intradermally (i.d.). When the $1^{st}$ tumor reached ~3 mm in average diameter, the $2^{nd}$ tumor ($5*10^4$ cells) was implanted on the left flank. Treatment was performed when the $1^{st}$ tumor reached 5.5 mm, while the $2^{nd}$ tumor was left untreated.

Because of its aggressive nature, only when tumors of both flanks were eliminated could the animal survived long term. All untreated animals reached their endpoint within 40 days as expected (FIG. 8). While ablation alone did lead to minimal long-term survival at ~14% (a compound of Formula 1 alone at ~9%), addition of a compound of Formula 1 (ablation+a compound of Formula 1) significantly improved the efficacy more than 3-fold, resulting in 57% long term survival (FIG. 8).

Figure 9:
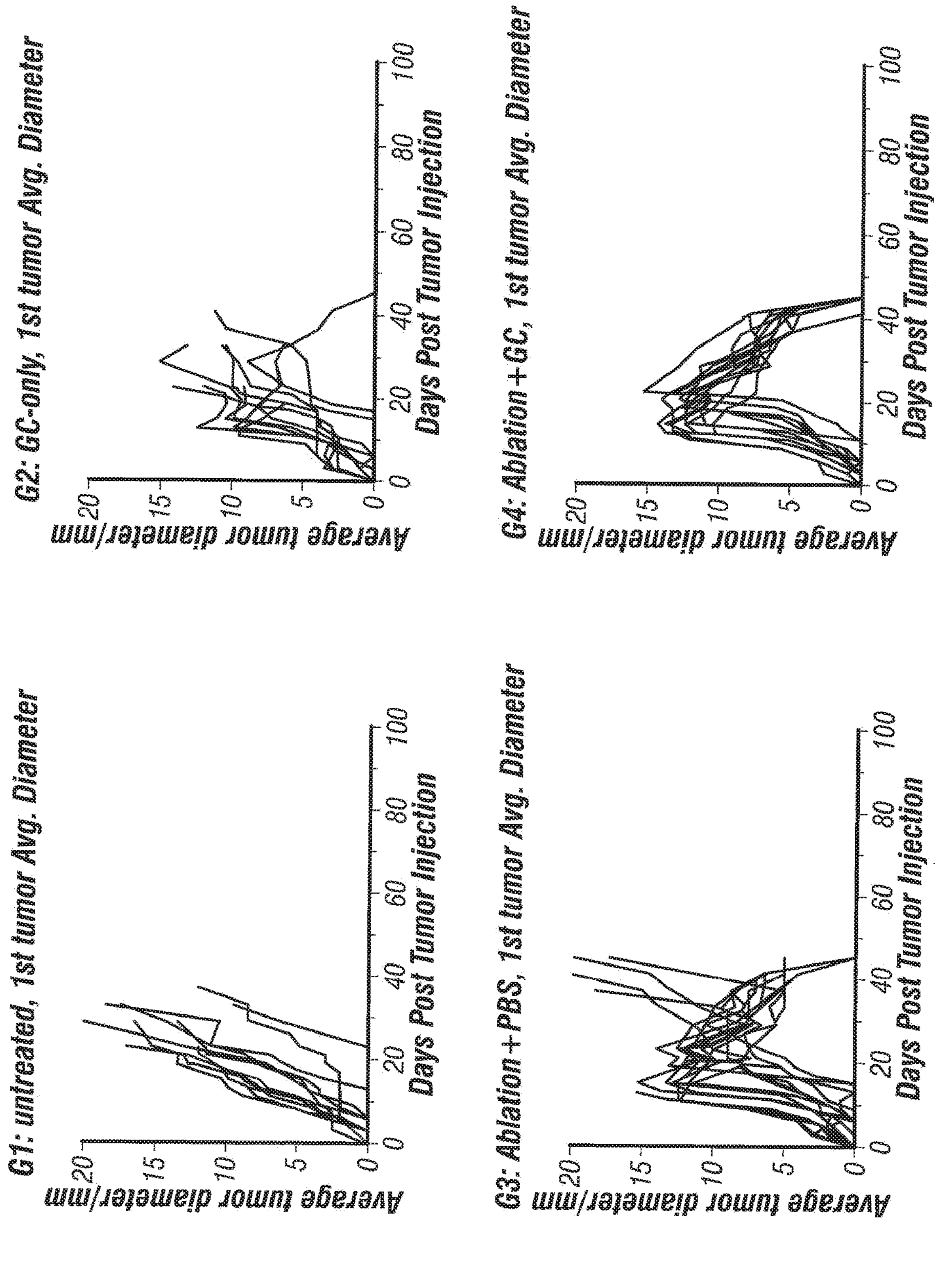
FIG. 9 is a graph showing growth of the $1^{st}$ tumors on the right flank that were treated directly.
Figure 10:
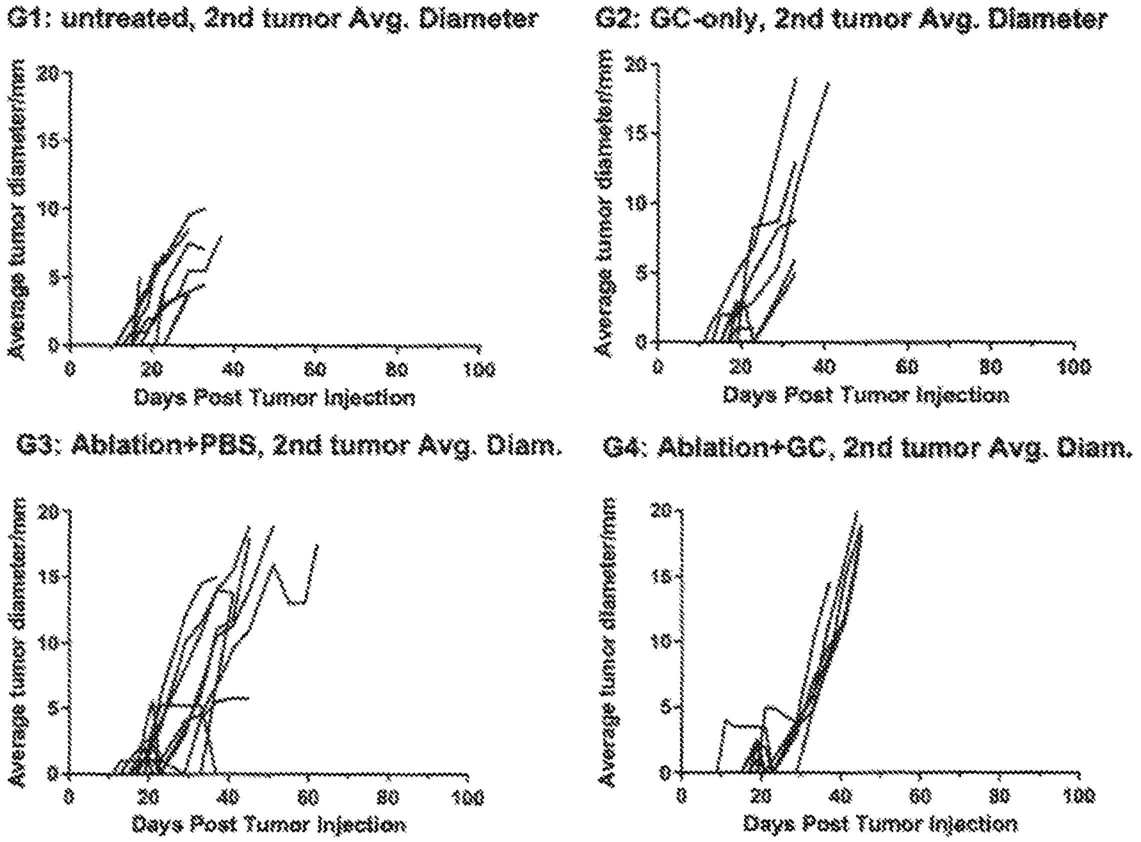
FIG. 10 is a graph showing growth of the $2^{nd}$ tumors on the contralateral flank (left) that was not treated directly.

A closer look at the growth of the tumors reveals that addition of a compound of Formula 1 to ablation enhanced elimination of tumor both locally at the treatment site (FIG. 9) and systemically at the untreated distant site (FIG. 10). Among the long-term survivors in the compound of Formula 1+ablation group (G4), the contralateral tumors demonstrated growth followed by regression or no growth at all, whereas in the untreated control, the tumors grew progressively. In the group that received ablation alone (G3), although some contralateral tumor did regress, only 2/14 animals eventually had both the primary and secondary tumor eliminated to allow long term survival. Because these $2^{nd}$ tumors were never treated directly, their growth delay/regression was not caused by the direct killing of ablation, but rather the downstream effects of the treatment. It is our hope that this abscopal effect could be replicated in the clinic for the systemic inhibition of metastatic lesions.

Figure 11:
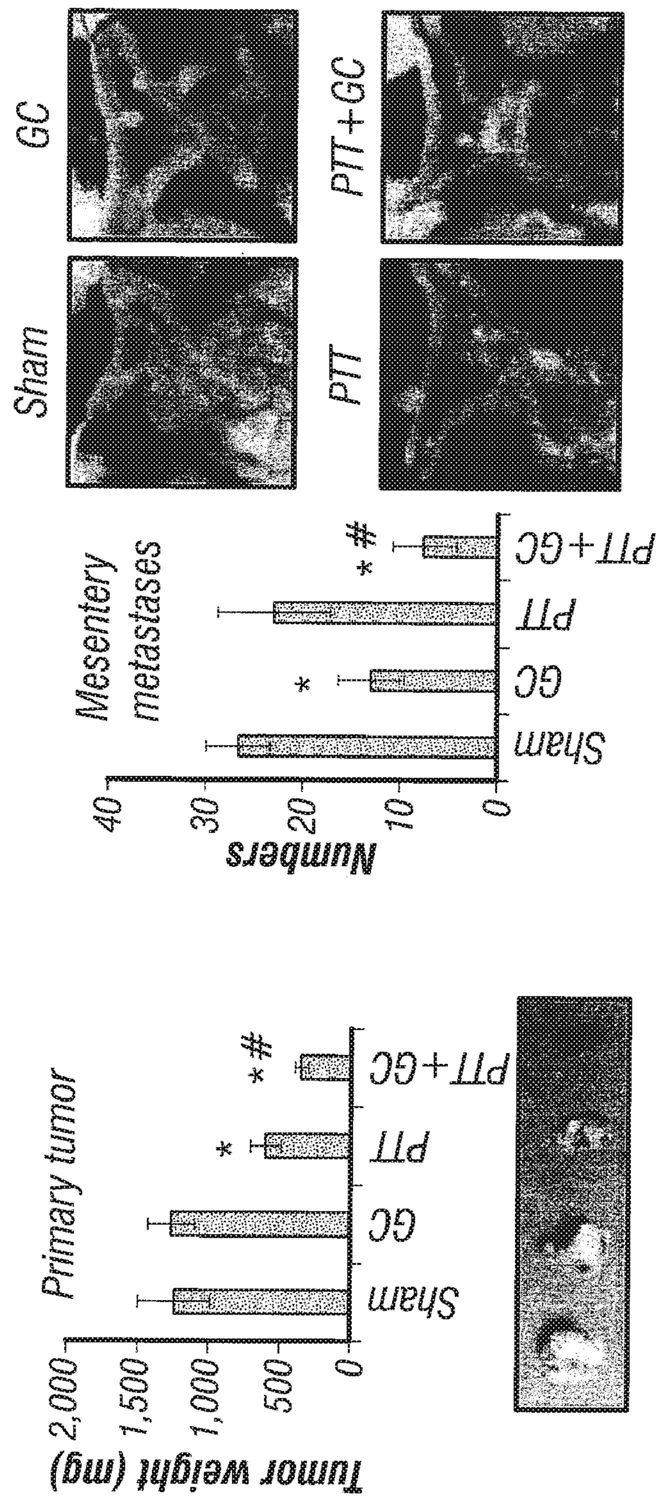
FIG. 11 is a graph showing growth of the Panc02-H7 tumor injected orthotopically into the pancreatic head. (Left) Primary tumor in the pancreas. (Right) Mesentery metastases.

In an aggressive orthotopic pancreatic cancer model, Panc02-H7 was injected into the pancreas and treated with interstitial thermal laser ablation+a compound of Formula 1. Orthotopic model has the advantage of more closely mimicking the true physiological niche where the studied tumor originates from, hence reflecting a more representative response to treatment. Primary tumor burden (FIG. 11, left) was reduced by ablation alone and further reduced by a compound of Formula 1. Ablation alone did not have significant impact on the extent of metastases but Ablation+a compound of Formula 1 lowered the number of metastatic lesions by almost 3 times (FIG. 11, right). Interestingly, a compound of Formula 1 alone, in spite of having no impact on primary tumor, reduced the metastasis by almost 50%. It is possible that a compound of Formula 1 has some unexplored inhibitory effects on tumor cells that have acquired metastatic capabilities.

Example 6

Use of Compositions of Formula 1 to Stimulate T Cell Response

A compound of Formula 1, described above, has been shown to enhance the efficacy of tumor ablation, both locally and systemically, when injected intratumorally in conjunction with the ablation procedure. Such improvement in efficacy requires the intact adaptive immune compartment as the benefits are abrogated in thymic nude mice that has an impaired T and B cell population. More specifically, in pancreatic cancer model Pan02-H7, increased infiltration of $CD8^+IFN\gamma^+$ and $CD4^+$ $IFN\gamma^+$ T cells was found in the contralateral tumor in treated animals together with elevated levels of serum IFNγ and TNFα. These data suggest that a compound of Formula 1 works at least in part by augmenting the initiation of anti-tumor T cell response (CTL and T-helper 1-skewed in particular). Furthermore, such effects are long lasting and cured animals are better protected against re-challenge of the same tumor compared to ablation alone.

To initiate a potent antitumor T cell response, one of the crucial steps involves antigen presenting cells APCs such as macrophages and dendritic cells DCs acquiring sufficient amount of tumor antigens, be properly activated and presenting these antigens to T and B cells after migration to the draining lymph node. As compounds of Formula 1 are injected locally in an ablated tumor where it will encounter incoming APCs as tumor antigens are released by the ablation. We have investigated whether compounds of Formula 1 have any directs effects on the functions of these APCs. In vitro works in macrophage cell line RAW264.7 demonstrated compounds of Formula 1 enhance macrophage functions including phagocytosis, NO production, TNFa production and expression of maturation markers CD80 and 86. In DC cell line DC2.4, experiments surprisingly show that compounds of Formula 1 activate dendritic cells, as opposed to GCs with $M_W$ of greater than 420 kDa, which can be measured by elevation of co-stimulatory marker CD40. CD40 signaling can also lead to upregulation of other co-stimulatory markers such as those in the B7 family. Taken together, it is likely that an important part of mechanism of action employed by compounds of Formula 1 is enhancing the activation and functions of APCs, which play a key role in initiating the downstream anti-tumor T cell response.

Example 7

Use of a Compound of Formula 1 to Activate Dendritic Cells

We made the wholly unexpected discovery that a compound of Formula 1 possesses properties that are significantly different from, and superior to, known GCs. As noted above, these superior properties include sterile filterability and discrepancy in molecular weight. In addition to the improved chemical structure and composition, we have made the highly unexpected discovery that compounds of Formula 1 are able to activate dendritic cells (DC), as compared to conventional GC with a $M_W$ of greater than 420 kDa. This was determined by measuring CD40 expression after co-incubating DC with a compound of Formula 1, versus conventional GC respectively. Without wishing to be bound by theory, we believe the expression of CD40 is one key aspect of compounds of Formula 1 mechanism of action.

Experimental Overview:

1. Culture DCs cell line DC 2.4 at $1*10^5$ cells in 0.2 ml D-10 media in 96-well U-bottom polystyrene plate. Split at least once before use.
2. Add GC into the wells and incubate cells overnight for 18-24 hrs.
3. Harvest cells and stain with anti-CD40 antibodies to measure the levels of DC activation by flow cytometry.

Readout:

CD40 expression as indicator of DC activation.

Results:

i) CD40 Expression on DCs was Upregulated by Compounds of Formula 1

Figure 5:
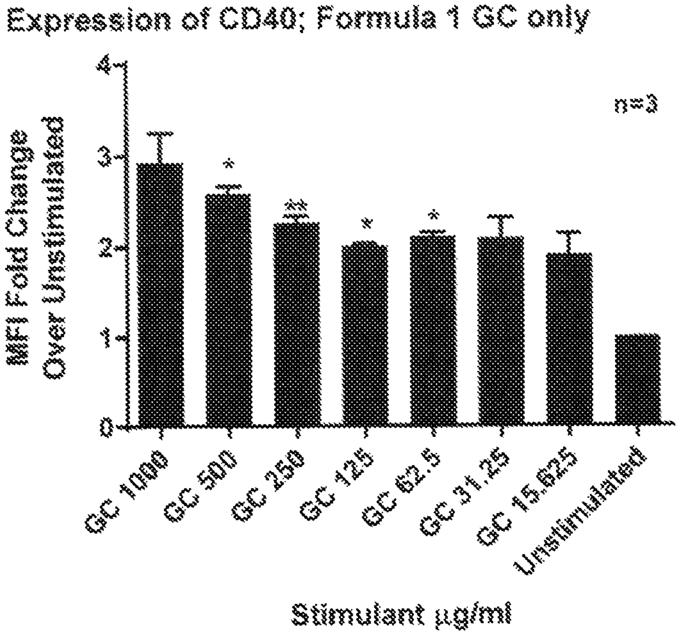
FIG. 5 is a bar graph showing expression of CD40 by DC2.4 stimulated with a compound of Formula 1 for 18 to 24 hours at different concentrations.
Figure 6:
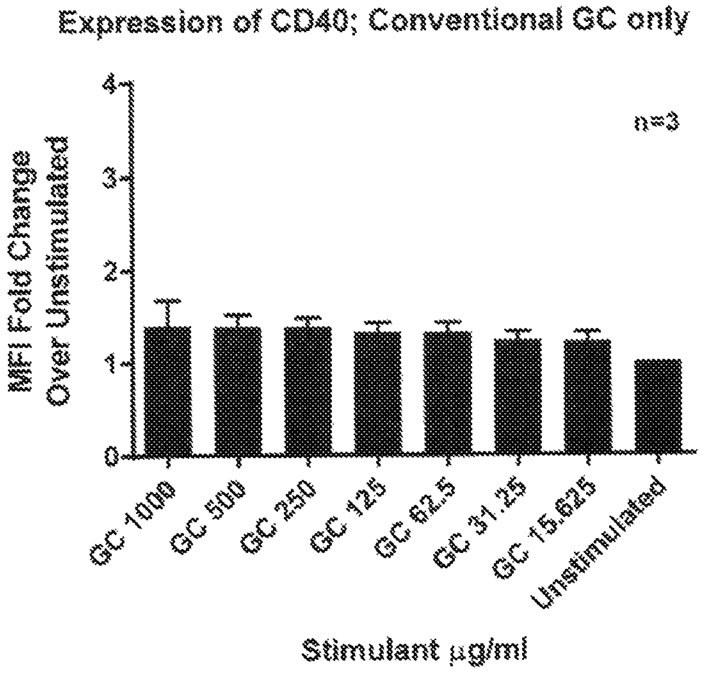
FIG. 6 is a bar graph showing expression of CD40 by DC2.4 stimulated by a conventional GC with a $M_W$ of 420 kDa for 18 to 24 hours at different concentrations.
Figure 7:
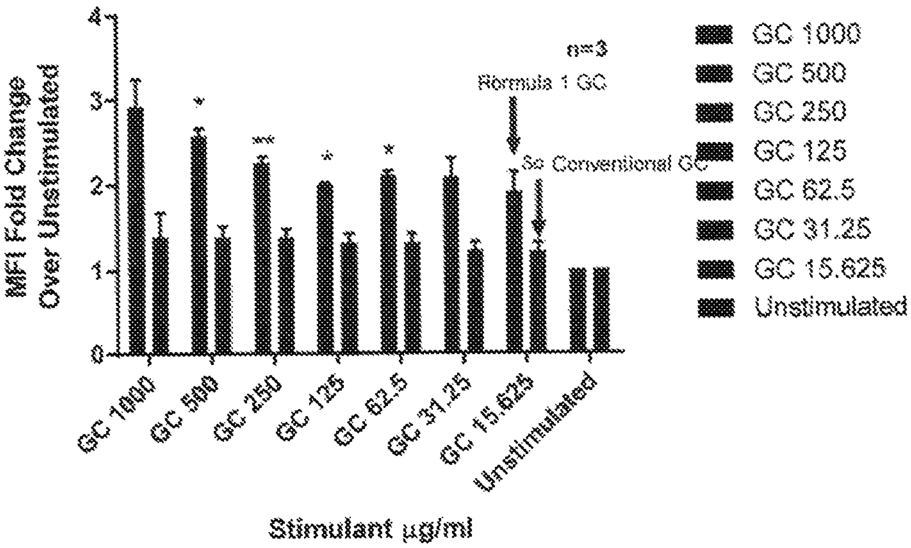
FIG. 7 is a bar graph showing expression of CD40 by DC2.4 stimulated with a compound of Formula 1 from FIG. 5, compared to a conventional GC with a $M_W$ of 420 kDa from FIG. 6, for 18 to 24 hours at different concentrations.

Three independent experiments were performed. In all cases, CD40 was upregulated by a compound of Formula 1 ($p<0.05$) in a dose dependent manner as demonstrated before. This demonstrates that compounds of Formula 1 are capable of activating DCs and stimulate their maturation. Positive control TLR4 ligand LPS induced ~14-fold increase of CD40 as expected and was not included in the graph for clarity. Isotype control was negative which rules out non-specific binding.

ii) CD40 Expression on DCs was Not Affected Upon In Vitro Stimulation of Conventional GC On the other hand, conventional GC with $M_W$ values greater than 420 kDa did not affect the expression of CD40 at the dose range tested, even when it was as high as 1000

μg/ml. This indicates the conventional GC was not capable of activating DCs as compounds of Formula 1 do in these experimental conditions. Data from FIG. 5 and FIG. 6 are plotted together on FIG. 7 for easier visual comparison. Furthermore, we believe that GC in conjunction with methods that induce immunogenic cell death, such as tumor ablation or radiation therapy, may dramatically improve the observable outcomes of checkpoint inhibitors and/or other immunotherapies for cancer that are T cell mediated, and thus provide an opportunity to design additional immunotherapies to treat proliferative disorders in human subjects.

Example 8

Combination with Checkpoint Inhibitors

Figure 13:
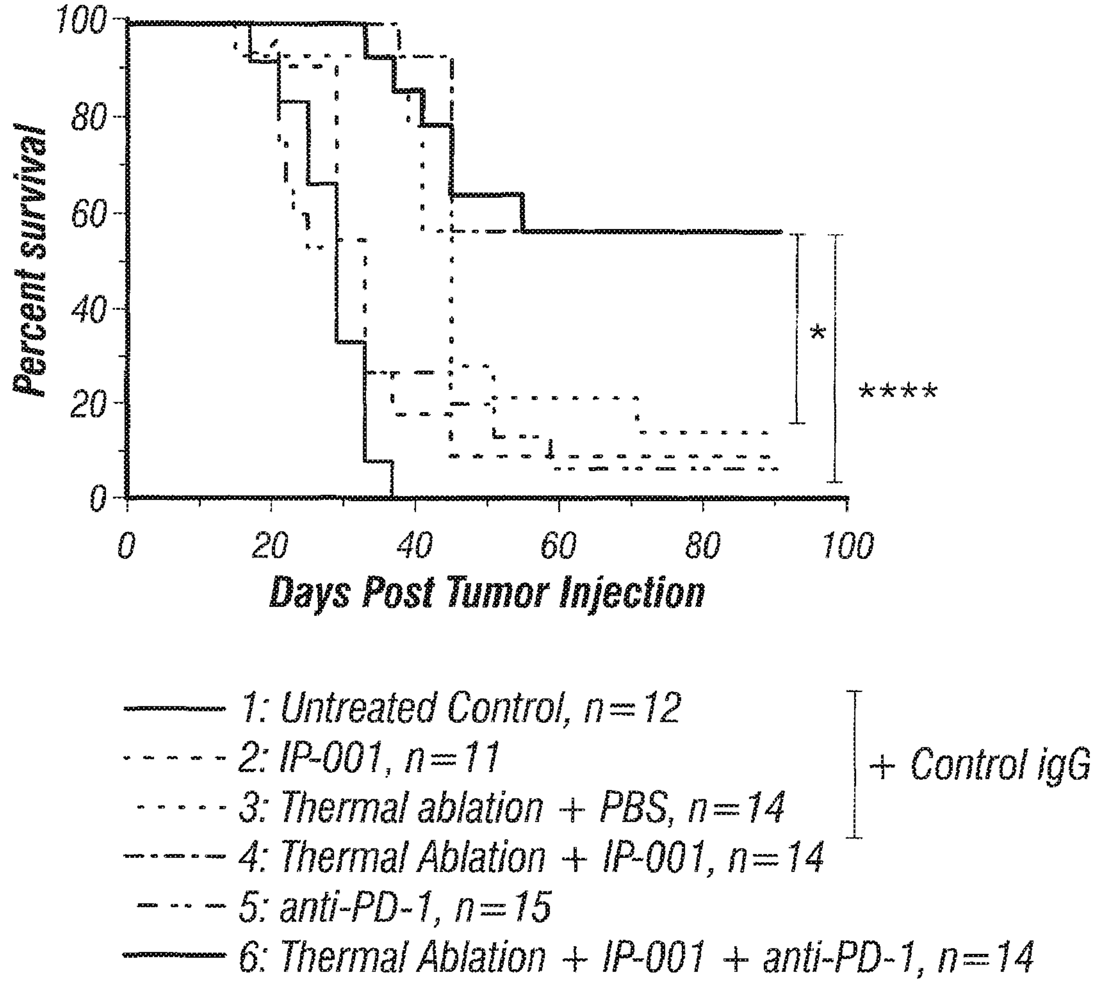
FIG. 13 is a graph showing survival of B16-F10 bearing animals post-treatment showing the Efficacy of the Formula 1 compound when administered in conjunction with either tumor ablation alone (G4), or tumor ablation and anti-PD1 (G6).

A compound of Formula 1, described above, when used in combination with checkpoint blockade antibodies anti-PD-1, has been shown to enhance the generation of memory response against the same tumor, when injected intratumorally in conjunction with the ablation procedure. As best illustrated in FIG. 13 in one experiment, two B16-F10 tumors were implanted in the C57BL/6 mice, one in each flank of the back ($2^{nd}$ tumor implanted when $1^{st}$ tumor was 3 mm). Only the $1^{st}$ tumor was treated with ablation+compound of Formula 1 at 5.5 mm, Group 4 (G4), the $2^{nd}$ tumor was left untreated. Anti-PD-1 was administered on Day 7, 10, 13, 16 after implanting the tumor in combination with the ablation+compound of Formula 1 (G6). Control groups include untreated (G1), compound of Formula 1 (G2), ablation (G3), anti-PD-1 (G5).

Among long term survivors, both the $1^{st}$ and $2^{nd}$ tumor has to be eliminated. In that regard, both ablation+compound of Formula 1 (G4) and both ablation+compound of Formula 1+anti-PD-1 (G6) are superior to the other groups. Although long term survival rate was the same between these two groups in the experiment, any delay in growth of $2^{nd}$ tumor among non-survivors would nevertheless indicate a stronger systemic anti-tumor response.

Figure 14:
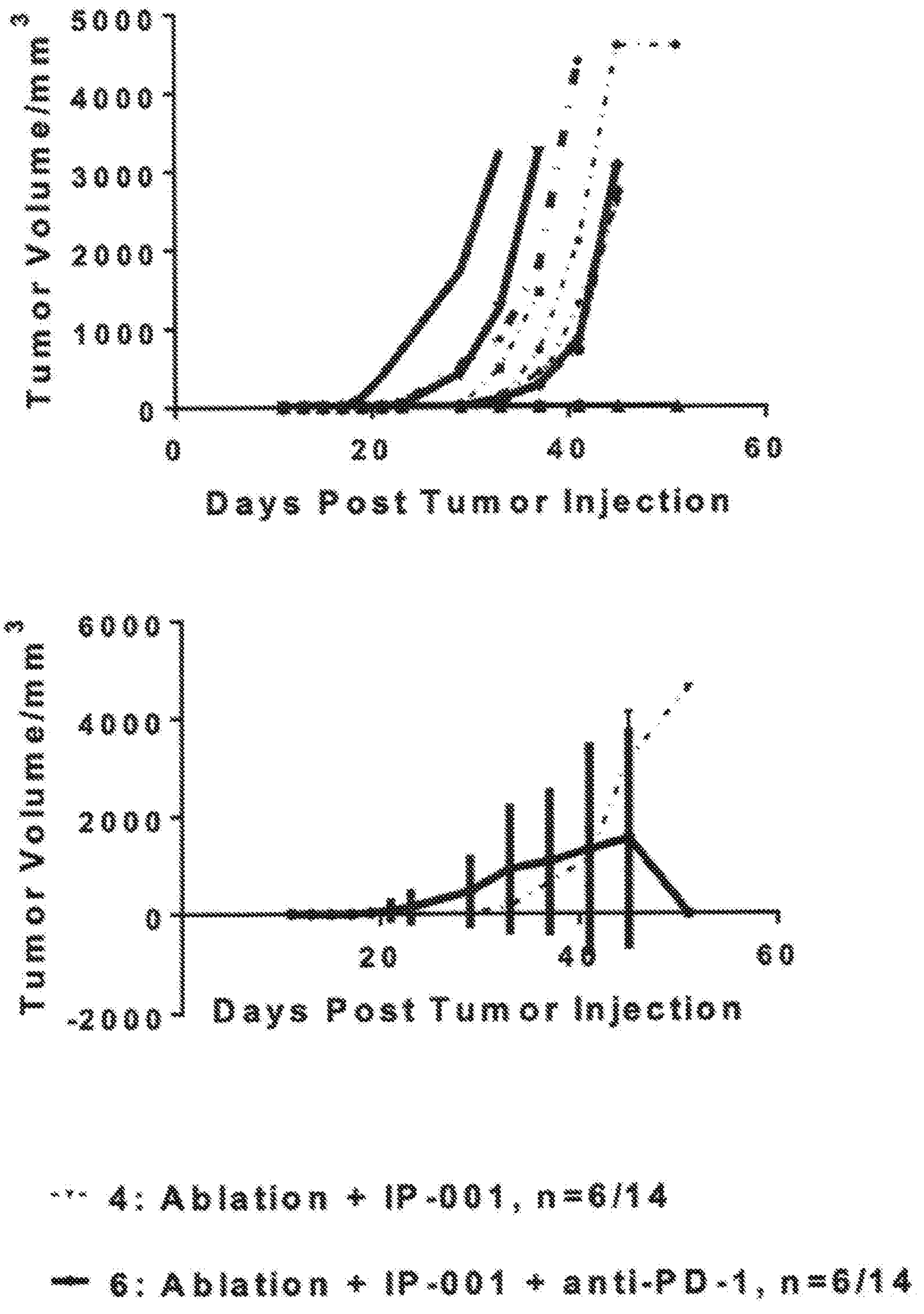
FIG. 14 illustrates two graphs comparing the growth of contralateral untreated tumor in non-survivors in G4 (ablation+compound of Formula 1) and G6 (ablation+compound of Formula 1+anti-PD1).
Figure 15:
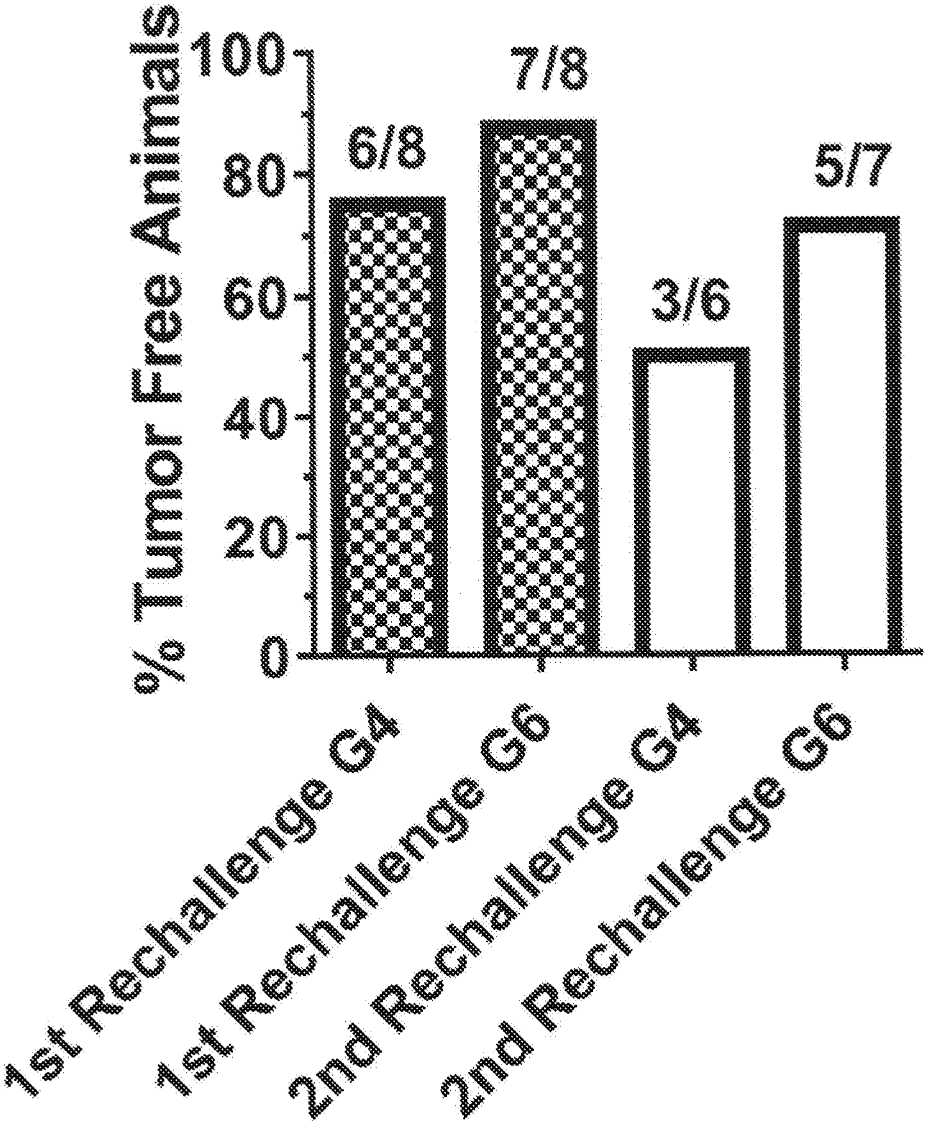
FIG. 15 is a bar graph showing percent surviving animals from G4 (ablation+compound of Formula 1) and G6 (ablation+compound of Formula 1+anti-PD1) protected from re-challenge of same B16-F10 tumors.

According to FIG. 14 this was the indeed the case. In the combination group G6, 3/6 of the $2^{nd}$ tumors showed delayed growth compared to ablation+compound of Formula 1 alone, and 2/6 even regressed (which was not seen in ablation+compound of Formula 1 alone). Because these $2^{nd}$ tumors were never treated directly, their growth delay/regression was work of systemic immune response. In other words, ablation+compound of Formula 1 and checkpoint inhibitor anti-PD-1 works synergistically and demonstrated a stronger initiating effect on systemic anti-tumor immunity. This combination advantage is to be further optimized with protocol modifications.

Referring now to FIG. 13, the survivors in G4 were then re-challenged on day 97 with the same tumor B16-F10 ($7.5*10^4$ cells). 75% (6/8) of animals of G4 (ablation+compound of Formula 1) withstood the re-challenge and remained tumor free for 30 days, compared to 87.5 (7/8) in the combination group 6 (G6; ablation+compound of Formula 1+anti-PD1). On Day 185, the survivors from the first re-challenge were challenged for a second time with double the dose of the tumor cells ($1.5*10^5$ cells). 50% (3/6) of animals of G4 withstood the re-challenge and remain tumor free for 30 days, compared to 71.4 (5/7) in the combination group 6 (G6).

Collectively, ablation+compound of Formula 1 and the combination of ablation+compound of Formula 1 and anti-PD-1 both generated long lasted memory against the tumor. Addition of anti-PD1 in the original treatment could thus enhance the generation of such memory response. Similar data was found in a separate experiment where anti-CTLA-4+anti-PD-1 checkpoint blockade combination was used instead of anti-PD-1 alone, as shown in FIG. 13.

Other Embodiments

From the foregoing description, it will be apparent to one of ordinary skill in the art that variations and modifications may be made to the embodiments described herein to adapt it to various usages and conditions.

We claim:

1. A method of treating a neoplasm comprising administering a sterile filtered glycated chitosan (GC) polymer and at least one checkpoint inhibitor comprising anti-PD-1 antibody or anti-PD-L1 antibody to a patient in need thereof; and treating the patient with ablation therapy, radiation therapy or cytotoxic therapy of the neoplasm, wherein the glycated chitosan polymer is represented by Formula 1:

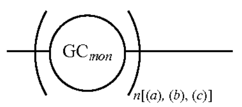

wherein n is the number of subunits, and (a), (b) and (c) represent the number of each of the Monomer subunits below comprising $GC_{mon}$:

Monomer (a)

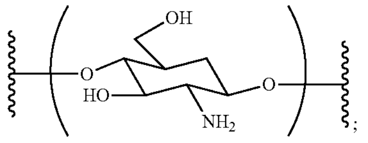

Monomer (b)

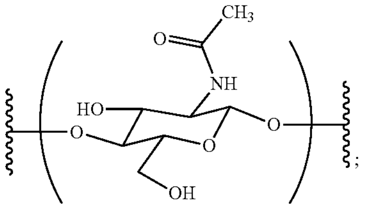

and

Monomer (c)

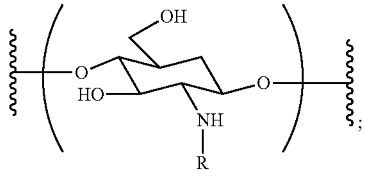

wherein R=substitution resulting from glycation; wherein n=3–1933, (a)=1–986, (b)=1–386, (c)=1–560) for a Mw (Molecular Weight) of less than 420 kDa; and a degree of glycation (DG) is of up to, but not including, 30 percent.

2. The method of claim 1, wherein the sterile filtered GC polymer has a MW of about 250 kDa, a DG of about 5%, and a DDA (degree of deacetylation) of about 80%.

3. The method of claim 1, wherein the sterile filtered GC polymer is formulated in a physiologically compatible carrier.

4. The method of claim 3, wherein the physiologically compatible carrier is an aqueous solution.

5. The method of claim 4, wherein the aqueous solution has a pH from between about 5 to about 7.

6. The method of claim 5, wherein the aqueous solution comprises one percent by weight of the GC polymer, and wherein the aqueous solution has a viscosity of between one to one hundred centistokes measured at 25 degrees Celsius.

7. The method of claim 1, wherein the at least one checkpoint inhibitor is the anti-PD-1 antibody.

8. The method of claim 1, wherein the radiation therapy comprises photon beam therapy or particle beam therapy.

9. The method of claim 1, wherein the glycated chitosan polymer is administered intratumorally.

10. The method of claim 1, wherein the sterile filtered GC polymer has a molecular weight of about 250 kDa.

11. The method of claim 1, wherein the sterile filtered GC polymer has a DG of about 0.5% to about 9.5%.

12. The method of claim 1, wherein the sterile filtered GC polymer has a DG of about 1% to about 8%.

13. The method of claim 1, wherein the sterile filtered GC polymer has a DG of about 3% to about 6%.

14. The method of claim 1, wherein the sterile filtered GC polymer has a DG of about 5%.

15. The method of claim 1, wherein the patient is treated with radiation therapy.

* * * * *